US007252953B2

(12) United States Patent
Suo et al.

(10) Patent No.: US 7,252,953 B2
(45) Date of Patent: Aug. 7, 2007

(54) METHOD OF DETECTING AND PREVENTING ALZHEIMER'S DISEASE, PARTICULARLY AT PRODROMAL AND EARLY STAGES

(75) Inventors: Zhiming Suo, Kansas City, KS (US); Barry W. Festoff, Kansas City, MO (US)

(73) Assignee: United States of America Department of Veterans Affairs, Washington, DC (US)

( * ) Notice: Subject to any disclaimer, the term of this patent is extended or adjusted under 35 U.S.C. 154(b) by 0 days.

(21) Appl. No.: 10/524,060

(22) PCT Filed: Aug. 12, 2003

(86) PCT No.: PCT/US03/32357

§ 371 (c)(1),
(2), (4) Date: Feb. 8, 2005

(87) PCT Pub. No.: WO2004/014296

PCT Pub. Date: Feb. 19, 2004

(65) Prior Publication Data

US 2005/0272025 A1    Dec. 8, 2005

Related U.S. Application Data

(60) Provisional application No. 60/402,701, filed on Aug. 13, 2002.

(51) Int. Cl.
*G01N 33/53* (2006.01)
(52) U.S. Cl. ....................................................... 435/7.1
(58) Field of Classification Search ................... None
See application file for complete search history.

(56) References Cited

U.S. PATENT DOCUMENTS 6,110,693 A    8/2000    Barak et al.

FOREIGN PATENT DOCUMENTS

WO    WO 99/27944    6/1999

OTHER PUBLICATIONS

Hardy et al. Science 2002. 297: 353-356.*
Braak, H. & Braak, E. Neuropathological stageing of Alzheimer-related changes. *Acta Neuropathol* (Berl) 82, 239-59 (1991).
Saitoh, T., Horsburgh, K. & Masliah, E. Hyperactivation of signal transduction systems in Alzheimer's disease. *Ann N Y Acad Sci* 695, 34-41 (1993).
Fowler, C.J., Cowburn, R.F., Garlind, A., Winblad, B. & O'Neill, C. Disturbances in signal transduction mechanisms in Alzheimer's disease. *Mol Cell Biochem* 149-150, 287-92 (1995).
Joseph, J.A., Cutler, R. & Roth, G.S. Changes in G protein-mediated signal transduction in aging and Alzheimer's disease. *Ann N Y Acad Sci* 695, 42-5 (1993).

Shimohama, S. et al. Aberrant phosphoinositide metabolism in Alzheimer's disease. *Ann N Y Acad Sci* 695, 46-9 (1993).
Matsushima, H., Shimohama, S., Chachin, M., Taniguchi, T. & Kimura, J. Ca2+-independent and Ca2+-dependent protein kinase C changes in the brain of patients with Alzheimer's disease. *J Neurochem* 67, 317-23 (1996).
Mattson, M.P. & Chan, S.L. Dysregulation of cellular calcium homeostasis in Alzheimer's disease: bad genes and bad habits. *J Mol Neurosci* 17, 205-24 (2001).
Fowler, C.J., Garlind, A., O'Neill, C. & Cowburn, R.F. Receptor-effector coupling dysfunctions in Alzheimer's disease. *Ann N Y Acad Sci* 786, 294-304 (1996).
Hisatomi, O. et al. A novel subtype of G-protein-coupled receptor kinase, GRK7, in teleost cone photoreceptors. *FEBS Lett* 424, 159-64. (1998).
Pitcher, J.A., Freedman, N.J. & Lefkowitz, R.J. G protein-coupled receptor kinases. *Annu Rev Biochem* 67, 653-92 (1998).
Sallese, M. et al. Regulation of G protein-coupled receptor kinase subtypes by calcium sensor proteins. *Biochim Biophys Acta* 1498, 112-21. (2000).
Bristow, M.R. et al. Beta-adrenergic pathways in nonfailing and failing human ventricular myocardium. *Circulation* 82, I12-25 (1990).
Ungerer, M., Kessebohm, K., Kronsbein, K., Lohse, M.J. & Richardt, G. Activation of beta-adrenergic receptor kinase during myocardial ischemia. *Circ Res* 79, 455-60 (1996).
Gros, R., Benovic, J.L., Tan, C.M. & Feldman, R.D. G-protein-coupled receptor kinase activity is increased in hypertension. *J Clin Invest* 99, 2087-93 (1997).
Premont, R.T., Inglese, J. & Lefkowitz, R.J. Protein kinases that phosphorylate activated G protein-coupled receptors. *Faseb J* 9, 175-82 (1995).
Chen, J., Makino, C.L., Peachey, N.S., Baylor, D.A. & Simon, M.I. Mechanisms of rhodopsin inactivation in vivo as revealed by a COOH-terminal truncation mutant. *Science* 267, 374-7 (1995).
Terwilliger, R.Z., Ortiz, J., Guitart, X. & Nestler, E.J. Chronic morphine administration increases beta-adrenergic receptor kinase (beta ARK) levels in the rat locus coeruleus. *J Neurochem* 63, 1983-6 (1994).
Barak, L.S., Warabi, K., Feng, X., Caron, M.G. & Kwatra, M.M. Real-time visualization of the cellular redistribution of G protein-coupled receptor kinase 2 and beta-arrestin 2 during homologous desensitization of the substance P receptor. *J Biol Chem* 274, 7565-9 (1999).

(Continued)

Primary Examiner—Janet L. Andres
Assistant Examiner—Chang-Yu Wang
(74) Attorney, Agent, or Firm—Dinesh Agarwal, P.C.

(57) ABSTRACT

A method of detecting Alzheimer's disease includes detecting a disruption or alteration in normal sub-cellular distribution of G-protein receptor kinases (GRKs), particularly GRK2 and GRK5. The disruption is caused by abnormal accumulation of soluble β-amyloid. The prevention or suppression of the disease progression at prodromal or early stages includes correction of GRK dysfunction.

10 Claims, 24 Drawing Sheets

OTHER PUBLICATIONS

Harlan, J.E., Hajduk, P.J., Yoon, H.S. & Fesik, S.W. Pleckstrin homology domains bind to phosphatidylinositol-4,5-bisphosphate. *Nature* 371, 168-70 (1994).

DebBurman, S.K., Ptasienski, J., Benovic, J.L. & Hosey, M.M. G protein-coupled receptor kinase GRK2 is a phospholipid-dependent enzyme that can be conditionally activated by G protein betagamma subunits. *J Biol Chem* 271, 22552-62 (1996).

Freeman, J.L., Pitcher, J.A., Li, X., Bennett, V. & Lefkowitz, R.J. alpha-Actinin is a potent regulator of G protein-coupled receptor kinase activity and substrate specificity in vitro. *FEBS Lett* 473, 280-4 (2000).

Roth, G.S., Joseph, J.A. & Mason, R.P. Membrane alterations as causes of impaired signal transduction in Alzheimer's disease and aging. *Trends Neurosci* 18, 203-6 (1995).

Price, D.L. et al. Sequestration of tubulin in neurons in Alzheimer's disease. *Brain Res* 385, 305-10 (1986).

Wallace, M.A. Effects of Alzheimer's disease-related beta amyloid protein fragments on enzymes metabolizing phosphoinositides in brain. *Biochim Biophys Acta* 1227, 183-7 (1994).

Mattson, M.P. et al. beta-Amyloid peptides destabilize calcium homeostasis and render human cortical neurons vulnerable to excitotoxicity. *J Neurosci* 12, 376-89 (1992).

Chishti, M.A. et al. Early-onset amyloid deposition and cognitive deficits in transgenic mice expressing a double mutant form of APP695. *J Biol Chem* 15, 276(24):21562-70 (2001).

Schutzer, W.E., Reed, J.f., Bliziotes, M. & Mader, S.L. Upregulation of G protein-linked receptor kinases with advancing age in rat aorta. *Am J Physiol Regul Integr Comp Physiol* 280, R897-903 (2001).

Griffin, W.S. et al. Glial-neuronal interactions in Alzheimer's disease: the potential role of a 'cytokine cycle' in disease progression. *Brain Pathol* 8, 65-72 (1998).

Suo, Z. et al. Participation of protease-activated receptor-1 in thrombin-induced microglial activation. *J Neurochem* 80, 655-66 (2002).

Crawford, F. et al. Alzheimer's beta-amyloid vasoactivity: identification of a novel beta- amyloid conformational intermediate. *FEBS Lett* 436, 445-8 (1998).

Tiruppathi, C. et al. G protein-coupled receptor kinase-5 regulates thrombin-activated signaling in endothelial cells. *Proc Natl Acad Sci U S A* 97, 7440-5 (2000).

Shapiro, M.J., Weiss, E.J., Faruqi, T.R. & Coughlin, S.R. Protease-activated receptors 1 and 4 are shut off with distinct kinetics after activation by thrombin. *J Biol Chem* 275, 25216-21. (2000).

Noda, M., Nakanishi, H., Nabekura, J. & Akaike, N. AMPA-kainate subtypes of glutamate receptor in rat cerebral microglia. *J Neurosci* 20, 251-8 (2000).

Hajjar, A.M., Ernst, R.K., Tsai, J.H., Wilson, C.B. & Miller, S.I. Human Toll-like receptor 4 recognized host-specific LPS modifications. *Nat Immunol* 3, 354-9 (2002).

Stanciu, M. et al. Persistent activation of ERK contributes to glutamate-induced oxidative toxicity in a neuronal cell line and primary cortical neuron cultures. *J Biol Chem* 275, 12200-6 (2000).

Iversen, L.L., Mortishire-Smith, R.J., Pollack, S.J. & Shearman, M.S. The toxicity in vitro of beta-amyloid protein. *Biochem J* 311, 1-16 (1995).

Meda, L. et al. Activation of microglial cells by beta-amyloid protein and interferon- gamma. *Nature* 374, 647-50 (1995).

Lue, L.F. et al. Soluble amyloid beta peptide concentration as a predictor of synaptic change in Alzheimer's disease. *Am J Pathol* 155(3):853-62 (1999).

Sigurdsson, E.M., Scholtzova, H., Mehta, P.D., Frangione, B. & Wisniewski, T. Immunization with a nontoxic/nonfibrillar amyloid-beta homologous peptide reduces Alzheimer's disease-associated pathology in transgenic mice. *Am J Pathol* 159, 439-47. (2001).

Lewis, J. et al. Enhanced neurofibrillary degeneration in transgenic mice expressing mutant tau and APP. *Science* 293, 1487-91 (2001).

Sandhu, F.A. et al. NMDA and AMPA receptors in transgenic mice expressing human beta- amyloid protein. *J Neurochem* 61, 2286-9. (1993).

Smith, D.H. et al. Brain trauma induces massive hippocampal neuron death linked to a surge in beta-amyloid levels in mice overexpressing mutant amyloid precursor protein. *Am J Pathol* 153, 1005-10 (1998).

Aragay, A.M. et al. Monocyte chemoattractant protein-1-induced CCR2B receptor desensitization mediated by the G protein-coupled receptor kinase 2. *Proc Natl Acad Sci U S A* 95, 2985-90 (1998).

Crawford, F., Suo, Z., Fang, C. & Mullan, M. Characteristics of the in vitro vasoactivity of beta-amyloid peptides. *Exp Neurol* 150, 159-68 (1998).

Suo, Z. et al. Soluble Alzheimers beta-amyloid constricts the cerebral vasculature in vivo. *Neurosci Lett* 257, 77-80 (1998).

Federal Interagency Forum on Aging-Related Statistics. 2000. Older Americans 2000: Key Indicators of Well-Being. Web site: agingstats.gov/chartbook2000/population.html. (Jan. 14, 2002.).

FMG Innovations dba Alzheimer's Test Kit. 2001. Early Alert Alzheimer's Home Screening Test. Apr. 23, 2001. Web site: alzheimerstestkit.com/(Oct. 8, 2001.).

Fraser P. E., G. Yu, L. Levesque, M. Nishimura, D.S. Yang, H. T. J. Mount, D. Westaway, and P. H. St-George-Hyslop. Feb. 2001. Presenilin function: connections to Alzheimer's disease and signal transduction. *Biochemical Society Symposia* 67:89-100.

Freeman J. L., E. M. De La Cruz, T. D. Pollard, R. J. Lefkowitz, and J. A. Pitcher. Aug. 7, 1998. Regulation of G protein-coupled receptor kinase 5 (GRK5) by actin. *Journal of Biological Chemistry* 273(32):20653-20657.

Market News Publishing Inc. 2001. Nycomed Amersham Imaging and Neurochem collaborate to create Alzheimer's diagnostic. *Intelihealth Inc.* Jul. 19, 2001. Web site: http://ipn.intelihealth.com/IPN/ihtIPN/WSIPN000/23883/7194/328776.html. (Oct. 8, 2001.).

McLean C. A., R. A. Cherny, F. W. Fraser, S. J. Fuller, M. J. Smith, K. Beyreuther, Al Bush, and C. L. Masters. Dec. 1999. Soluble pool of Aβ amyloid as a determinant of severity of neurodegeneration in Alzheimer's disease. *Annals of Neurology* 46:860-866.

Medical Devicelink, 1997. Test developers pursue early Alzheimer's disease diagnostic. *IVD Technology Magazine*. Mar. 1997. Web site: devicelink.com/ivdt/archive/97/03/003.html. (Oct. 8, 2001.).

National Institute on Aging. 2001. *Alzheimer's Disease Fact Sheet*. Alzheimer's Disease Education & Referral Center, National Institute on Aging, National Institutes of Health, 2001. Web site: http://www.alzheimers.org/pubs/adfact.html (Dec. 5, 2002.).

National Institutes of Health. 1994. *Alzheimer's Disease*. Web site: pueblo.gsa.gov/cic_text/health/alzheim/alzheim.htm. (Oct. 8, 2001).

Neve R. L., D. L. McPhie, and Y. Chen. Feb. 2001. Alzheimer's disease: dysfunction of a signalling pathway mediated by the amyloid precursor protein? *Biochemical Society of Symposia* 67:37-50.

O'Neill C., R. F. Cowburn, W. L. Bonkale, T. G. Ohm, J. Fastbom, M. Carmody, and M. Kelliher. Feb. 2001. Dysfunctional intracellular calcium homoeostasis: a central cause of neurodegeneration in Alzheimer's disease. *Biochemical Society Symposia* 67:177-194.

Pitcher J. A., R. A. Hall, Y. Daaka, J. Zhang, S. S.G. Ferguson, S. Hester, S. Miller, M. G. Caron, R. J. Lefkowitz, and L. S. Barak. May 15, 1998. The G protein-coupled receptor kinase 2 is a microtubule-associated protein kinase that phosphorylates tubulin. *Journal of Biological Chemistry* 273(20):12316-12324.

Silva, Chris. 2001. Joining the great chase: Rockville biotech firm is among those racing to find an Alzheimer's cure. *Washington Business Journal*. May 25, 2001. Web site: http://washington.bcentral.com/washington/stories/2001/05/28/focus1.html. (Oct. 8, 2001.).

Strittmatter W. J. Feb. 2001. Apolipoprotein E and Alzheimer's disease: signal transduction mechanisms. *Biochemical Society Symposia* 67:101-109.

Suo Z., M. Wu, S. Ameenuddin, H. E. Anderson, J. E. Zoloty, B. A. Citron, P. Andrade-Gordon, and B. W. Festoff. Feb. 2002. Participation of protease-activated receptor-1 in thrombin-induced microglial activation. *Journal of Neurochemistry* 80(4):655-666.

Cowburn et al., Receptor-G-protein signalling in Alzheimer's disease. Biochem. Soc. Symp., 2001, vol. 67, pp. 167-175.

Penn et al., Regulation of G-protein coupled receptor kinases. Trends Cardiovascul. Med., 2000, vol. 10,No. 2, pp. 81-89.

Murphy et al., Development of a monoclonal antibody specific for the COOH-terminal of beta-amyloid 1-42 and its immunochemical reactivity in Alzheimer's disease and related disorders. American J. Pathology, 1994, vol. 144, No. 5, pp. 1082-1088.

\* cited by examiner

METHOD OF DETECTING AND PREVENTING ALZHEIMER'S DISEASE, PARTICULARLY AT PRODROMAL AND EARLY STAGES

CROSS-REFERENCE TO RELATED APPLICATIONS

The present application claims priority on prior U.S. Provisional Application Ser. No. 60/402,701, filed Aug. 13, 2002, and which is incorporated herein in its entirety by reference.

STATEMENT REGARDING FEDERALLY SPONSORED RESEARCH OR DEVELOPMENT

The work leading to the present invention was supported by one or more grants from the U.S. Government. The U.S. Government therefore has certain rights in the invention.

BACKGROUND OF THE INVENTION

The present invention is directed to detecting and treating Alzheimer's disease, and more particularly to the detection and prevention of Alzheimer's disease at prodromal and early stages.

Alzheimer's disease (AD) is the most common neurodegenerative disorder affecting millions of elderly world-wide and desperately demands both specific prevention for future victims and effective therapies for those currently suffering. It results in memory loss, behavior and personality changes, and a decline in thinking abilities. It is believed that up to 4 million Americans suffer from AD. The disease usually begins after age 60, and the risk goes up with age. The number of people with AD doubles every 5 years beyond age 65. An estimated 35 million people or 13 percent of the total US population are now aged 65 or older and this percentage is expected to increase rapidly when the first baby boomers reach age 65. The estimated annual national cost of caring for AD patients is $100 billion (National Institute on Aging 2001). Amyloid plaques (SPs) and neurofibrillary tangles (NFTs) within the brain are the hallmark signs of AD. Unfortunately, the presence of these structures has been subject to confirmation only post mortem.

However, limited understanding of the pathogenesis, especially in prodromal and early stages, has largely hampered the continuing efforts in this regard. Although clinicians are increasingly making the diagnosis of mild cognitive impairment (MCI) commensurate evidence histologically and biochemically is lacking. Common in advanced AD brains are SPs and NFTs, the pathological hallmarks of AD (Reference 1). Closely associated with these pathologic changes are apparent signal transduction system aberrancies (References 2-3). In more detail, these disturbances have concentrated on various G-protein coupled receptors (GPCRs) (Reference 4) and their downstream effectors, such as phosphoinositide metabolism (Reference 5), protein kinase C activity (References 2 and 6) and calcium homeostasis (Reference 7). Several authors have pointed out that the locus of the signal transduction deficits appears to be at the receptor-G protein interface (References 4 and 8), where uncoupling of a GPCR at its C-terminus to its specific GTPase normally occurs, although specific responsible molecules remain to be identified.

GPCRs comprise one of the largest gene families in the human genome, and mediate a huge variety of cellular functions regulated by neurotransmitters, hormones, chemokines, and many other molecules. Timely uncoupling of GPCR signaling is crucial for maintaining appropriateness and integrity of the GPCR-mediated physiological functions. This uncoupling is primarily mediated by a much smaller gene family, currently numbering seven members, of GPCR kinases (GRKs) (References 9-10). The specificity for a few GRK members to regulate a huge numbers of GPCRs is controlled in an agonist-dependent manner. In another words, GRKs preferentially bind to and phosphorylate agonist-occupied GPCRs to uncouple receptor from corresponding G-protein, a process known as homologous desensitization (Reference 11). Based on structural similarities, seven known GRK members are classified into four subfamilies (GRK1, GRK2/3, GRK4/5/6 and GRK7), with GRK2/3 and GRK5/6 having ubiquitous distributions including brain (References 9-10). Dysregulation of GRK2, probably GRK5 as well, has been implicated in the pathogenesis of chronic heart failure (Reference 12), myocardial ischemia (Reference 13), and hypertension (Reference 14), etc. cardiovascular disorders, where the GRKs have been extensively studied (Reference 10). Failure to desensitize rhodopsin signaling by GRK1 (Reference 15) can lead to photoreceptor cell death, and is believed to contribute to retinitis pigmentosa (Reference 16). In addition, increased GRK2 levels have been associated with opiate addiction (Reference 17). Aside from these, however, roles of GRKs in many other pathological conditions potentially associated with GPCR deregulation, such as in AD, remain virtually unexplored.

Due to the membrane location of GPCRs, GRK's retention on the plasma membrane or in the cytosoal physically affects its access and binding to GPCRs. In resting cells, GRK4 subfamily members (including GRK4/5/6) are tightly associated with the plasma membrane (Reference 10), while GRK2 subfamily members (GRK2/3) are primarily cytosolic and translocate to the membrane when cells are stimulated by GPCR agonists (References 10 and 18). However, in active cells, subcellular localization of GRKs appears to be determined by the content and capacity of GRK-binding factors in membrane versus cytosol. Phospholipids, particularly phosphatidylinositol-4,5-biphosphate ($PIP_2$), appear to be essential for GRKs to adhere to the membrane and bind GPCRs (Reference 19), while phosphatidylserine (PS) may also enhance GRK2 binding to GPCRs on the membrane (Reference 20). On the other hand, calcium/calmodulin and other calcium-binding proteins, as well as actin, actinin, etc. may contribute to sequester GRKs in the cytosol and inhibit binding of GRKs to GPCRs (References 11 and 21). In AD brains, significant membrane alterations (Reference 22), aberrant phosphoinositide metabolism (Reference 5), disrupted calcium homeostasis (Reference 7) and disorganized cytoskeleton proteins (Reference 23) could all influence the subcellular distribution of GRKs. In addition, increased β-amyloid (Aβ), a hydrophobic peptide central to AD pathogenesis, has been shown to decrease membrane $PIP_2$ (Reference 24) and increase $[Ca^{2+}]_i$ (Reference 25). Taken together, these findings have led us to investigate whether GRKs may contribute to the signal transduction system disturbances in AD brains. If yes, whether abnormal accumulation of Aβ might contribute to GRK dysregulation in the pathogenesis of AD. As a first attempt to answer these questions, we examined the expression and subcellular distribution of GRK2 and GRK5 in autopsied AD brains and in an early onset AD transgenic model, CRND8 mice. We also pursued further mechanistic studies in cultured murine microglial cells by investigating the impact of Aβ on GRK subcellular localization and regulation of GPCR signaling.

Currently there are no diagnostic methods available in the market that can detect AD accurately and reliably. The only accurate method now available is by postmortem examination of the brain.

Nymox, Inc. has developed a test called AlzheimAlert® that measures the amount of cerebrospinal fluid of a brain protein known as AD7C-NTP (neural thread protein) that is found in higher-than-normal concentrations in Alzheimer's patients. This urine test is considerably cheaper than any other test currently on the market, and the company claims over 90 percent accuracy. Even though the company received FDA clearance, it has experienced difficulty gaining industry acceptance (Medical Devicelink 1997).

FMG Innovations, Inc. recently released the Early Alert Alzheimer's Home Screening Kit. This self-administered test uses 12 scent strips to screen patients. According to the company, a decrease in the sense of smell is one of the early indicators of AD (FMG Innovations 2001).

Neurochem, Inc. and Nycomed Amersham Imaging announced an agreement to develop a product for the diagnosis of Alzheimer's disease. The companies will use Neurochem's proprietary molecule as a basis, and work together to design a system that will detect the presence of amyloid plaques in the brain. It is anticipated that the successful completion of the project will result in a product capable of accurately detecting early-stage Alzheimer's disease (Market News Publishing Inc. 2001).

Currently, there are no drugs available in the market to stop the progression of Alzheimer's disease. The drugs that are being marketed are agents for symptomatic treatment and/or to slow the progression of the disease.

Antipsychotic agents are often used to treat some of the symptoms experienced by patients with senile dementia brought on by AD. The leading drugs in this market are: tacrine (Cognex®) from Warner Lambert; donepezil (Aricept®) from Eisai (co-marketed by Pfizer), and galantamine HBr (Reminyl®), developed by Shire and to be marketed by Janssen Pharmaceutica Products, L.P. All three products can act as acetylcholinesterase inhibitors and are used to treat the memory/cognitive impairment that is often the earliest sign of AD.

OBJECTS AND BRIEF SUMMARY OF THE INVENTION

The principal object of the present invention is to uncover the mechanisms that manifest Alzheimer's pathogenesis, particularly at prodromal and early stages, so as to provide molecular basis for developing specific early diagnostic means and preventive and/or therapeutic approaches. This is based, at least in part, on the discovery that dysfunction of G-protein coupled receptor kinases (GRKs), particularly GRK2 and GRK5, occurs in brains with Alzheimer's disease. The data/evidence presented in this invention directly links soluble beta-amyloid (sAβ) to GRK dysfunction both at early time points before the disease occurs in a transgenic model and until the end stages of the disease as was found in postmortem brains.

Another object of the present invention is to provide a method of detecting Alzheimer's pathogenesis, particularly at prodromal or early stages.

Yet Another object of the present invention is to provide a method of inhibiting GRK-GPCR interaction/binding in cells.

Still yet another object of the present invention is to provide a method of inhibiting desensitization of GPCR in cells.

An additional object of the present invention is to provide a method of preventing or suppressing Alzheimer's disease progression at prodromal or early stages.

In summary, the present invention provides a molecular mechanism that methods for detecting prodromal or early Alzheimer's disease, and corresponding preventive and therapeutic approaches can be developed thereby.

The timely uncoupling of G-protein coupled receptor (GPCR) signaling, primarily by GPCR kinases (GRKs), is crucial for maintaining appropriateness and integrity of a large variety of GPCR-mediated physiological functions. The present invention reports the discovery that the plasma membrane content of the two most ubiquitously distributed GRK isoforms, GRK2 and GRK5, was significantly reduced in Alzheimer's disease (AD) brains. More importantly, as evidenced by an early-onset AD transgenic model, CRND8 mice, such abnormal GRK changes took place prior to cognitive decline while soluble β-amyloid (sAβ) levels were already significantly elevated in brain. Furthermore, we discovered that sAβ reduced membrane GRK5 content in cultured microglial cells and disrupted GRK-GPCR binding, an essential step for initiating GPCR desensitization. Consequently, GPCR signaling was prolonged and ultimately resulted in an increase of microglial tumor necrosis factor-α production. These results implicate GRK dysfunction and consequent cellular sensitization to GPCR activators as early pathogenetic events associated with sAβ accumulation at prodromal and early stages of AD.

At least one of the above objects is met, in part, by the present invention, which in one aspect links GRK dysfunction and cellular sensitization to GPCR activators to early Alzheimer's pathogenesis.

Another aspect of the present invention includes a method of detecting Alzheimer's pathogenesis by detecting a disruption in normal cellular distribution of a G-protein receptor kinase (GRK).

Another aspect of the present invention provides a preventive and therapeutic target. In other words, correction of the GRK dysfunction is believed to prevent the disease at prodromal stage, or stop or suppress the disease progression at early stages.

Another aspect of the present invention includes a method of detecting Alzheimer's pathogenesis by detecting abnormal cellular accumulation of β-amyloid in a subject suspect of having Alzheimer's disease.

Another aspect of the present invention includes a method of inhibiting GRK-GPCR interaction in a cell by pretreating the cell with a peptide, such as β-amyloid.

Another aspect of the present invention includes a method of inhibiting desensitization of GPCR in a cell by pretreating the cell with a peptide, such as β-amyloid.

Another aspect of the present invention includes a method of preventing or suppressing Alzheimer's disease progression at prodromal or early stages by correcting GRK dysfunction in cells.

Another aspect of the present invention includes a method of correcting soluble β-amyloid induced GRK dysfunction in cells by administering to a subject in need thereof a suitable amount of soluble β-amyloid antagonist.

Another aspect of the present invention includes a vaccine including a β-amyloid analog for use as prophylaxis against β-amyloid induced reaction in a subject.

BRIEF DESCRIPTION OF THE DRAWINGS

The above and other objects, novel features and advantages of the present invention will become apparent from the following detailed description of the invention, as illustrated in the drawings, in which.

DETAILED DESCRIPTION OF THE INVENTION

Figure 1A:
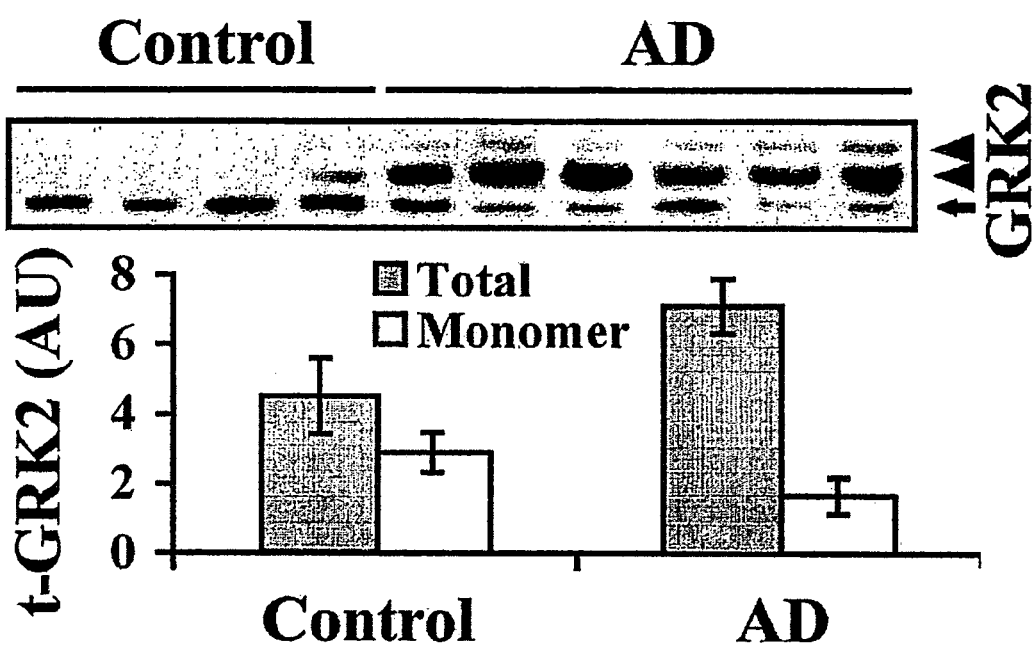
FIGS. 1A-D illustrate expression and subcellular distribution of GRK2 and GRK5 in postmortem AD brains.

The present invention is based, at least in part, on the discovery that dysfunction of G-protein coupled receptor kinases (GRKs) particularly GRK2 and GRK5, occurs in brains with Alzheimer's disease.

AD is a neurodegenerative disorder, with prominent pathological features involving the abnormal accumulation of a small peptide, termed β-amyloid (Aβ). However, the pathogenetic mechanisms associated with the abnormal Aβ accumulation remain unclear, which has significantly hampered understanding of the prognosis, prophylaxis and therapeutics for AD. In this regard, the current invention discovered an important pathogenetic change (GRK dysfunction) that is tightly associated with low concentrations of soluble Aβ that escalate prior to the disease onset and remain elevated during the disease progression. In detail, a small family of protein kinases known as GRKs, normally regulate a large group of cell signaling molecules, the GPCRs, by binding to and phosphorylating the activated GPCR so as to terminate the GPCR-mediated signaling. This process is called desensitization of GPCR signaling, normally occurring in every single cell type all the time to maintain the cell functioning properly. However, when soluble Aβ accumulates above physiological levels, it inhibits GRK function by impairing GRK-GPCR binding, thus causing cellular hyper-reactivity to GPCR stimuli. In microglial cells, this leads to an over-reactive proinflammatory reaction, resulting in inflammation-mediated neuronal degeneration. The same mechanism operates in neurons, the over-amplified and prolonged physiological (survival) signaling may be converted to pathological (death) signaling. While in peripheral cells, it may contribute to decreasing cerebral blood flow and disrupting the blood brain barrier, along with hyper-reactivity of circulating macrophages and/or leukocytes.

The totality of cellular functions, up to and including those controlling life and death, are tightly controlled by a large variety of balanced signals. Numerous examples are known in neural cells. For example, the failure to desensitize rhodopsin signaling leads to prolonged single photon responses, that are ultimately responsible for photoreceptor cell death in retinitis pigmentosa (Reference 16). Furthermore, although p44/42 MAPK activation is often attributed strictly to cell survival and proliferation, improperly persistent p44/42 MAPK activation can also contribute to neuronal cell death (Reference 35). Our recent studies indicate that although activation of both PAR1 and PAR4 by thrombin leads to p44/42 MAPK activation, since PAR1 signaling is rapidly shut off while PAR4 signaling persists, only PAR4, but not PAR1, activation contributes to thrombin-induced TNF-α release in microglial (Reference 29). These examples all suggest that, loss of GPCR signaling integrity and appropriateness could convert a physiological function to a pathophysiological one. In the present invention, we show that the subcellular distribution of the two most ubiquitously expressed GRK isoforms, GRK2 and GRK5, was disrupted in human AD brains. This disruption is one that appears not only in late stages of this devastating disease in human victims, but is also operative in prodromal stages of the disease as modeled in an AD Tg mouse line (Tg-CRND8). The subcellular localization for GRK access to membrane-bound GPCR substrates is the most important known regulatory feature of these enzymes (Reference 15). Therefore, reduction of membrane-associated GRKs in the AD brain may imply a general deficiency of GPCR desensitization by GRKs in the disease pathogenesis.

Multiple lines of evidence centralize a primary role for abnormal Aβ accumulation in AD, but the molecular mechanisms by which Aβ drives the disease pathogenesis remain obscure. Using cultured microglia as an in vitro model, we discovered that sAβ increased membrane-GRKs disassociation at nM concentrations, that in turn, inhibited GRK-GPCR interactions. The result of this was prolongation of GPCR signaling and enhancement of GPCR agonist-induced TNF-α production. In vivo, the increased TNF-α could contribute to the inflammatory pathology and neurodegeneration extensively observed in AD. More importantly, our findings provide the first evidence that directly links sAβ to GRK dysfunction, indicating that abnormal Aβ accumulation may be one of the causes for the GRK deficiency found in AD brains and the Tg model in vivo.

On the other hand, AD is a multifactorial disorder, and attempting to explain the disease pathogenesis with any single factor alone may be overly simplistic. When Aβ accumulates to very high concentrations and forms insoluble Aβ fibrils, it may directly contribute to certain aspects of AD pathology, such as direct neurotoxicity and microglial activation (References 36-37). However, prior to becoming highly concentrated and forming insoluble fibrils, the moderate increase of sAβ before the disease onset, as seen in the Tg-CRND8 mice and retention of the ~30% sAβ up to the end stages of the disease (References 36-37), may also play significant roles in the disease pathogenesis (References 38-39). Although the pathogenic effects of low dose sAβ may not be as apparent and direct as those found with insoluble Aβ fibrils (i.e., nM sAβ was not sufficient to directly induce TNF-α release from microglia as shown in this study (FIG. 6) while μM fibrillar Aβ was (Reference 37)), the sAβ-induced GRK dysfunction appears to be more fundamental, and likely to alter general cellular reactivity/vulnerability to a large variety of insults or even normal physiological signals. If Aβ is the primary causal factor for AD, the sAβ-induced GRK dysfunction may provide a critical novel platform to investigate interactions between the primary and various secondary factors implicated in AD pathogenesis.

METHODS

Cell Culture and Treatments

Primary microglial cultures were prepared from neonatal mouse (C57BL6) brains as previously described (Reference 29) and maintained in Delbecco's modified Eagle's medium with F-12 nutrient mixture (DMEM/F12) containing 10% fetal bovine sera (FBS) and antibiotics. N9 clonal murine microglial cell cultures were maintained in Iscoves modified Delbecco's medium (IMDM) containing 5% heat-inactivated FBS, 2 mM L-glutamine, 50 µM 2-mercaptoethanol and antibiotics. Treatment of both primary and N9 microglial cells were performed under serum-free conditions. Freshly solublized Aβ (BioSource, Camarillo, Calif.) peptides were prepared and characterized as previously described (References 30 and 44) and were used in all in vitro experiments. Unless specified, cells were always pretreated with sAβ for 5 min and then followed by challenge with α-thrombin (100 nM or as indicated), glutamate (2 mM) or LPS (5 ng/ml).

$Ca^{2+}$ Imaging

We measured $[Ca^{2+}]_i$ in microglial cells using Fluo-4 (2 µM) with the aid of a Nikon BioRadiance triple laser scanning confocal microscope. Image collection, quantification and data analysis were performed as previously described (Reference 29).

Immunoprecipitation (IP) and Western Blot (WB) Analysis

Cultured cells were lysed in pre-chilled 2×IP buffer I (Tris, 20 mM, pH 7.4; NaCl, 300 mM; EDTA, 2 mM; 2 mM EGTA, pH 8.0; 0.4 mM sodium ortho-vanadate, 2% Triton X-100; 1% NP-40; 0.4 mM PMSF) supplemented both with phosphatase and protease inhibitor cocktails. After centrifugation, the supernatants were collected and total protein concentrations were determined by the bicinchoninic acid assay (BCA). Equal amounts (250 µg) of cell lysates from each group were mixed with 20 µl (~5 µg) of either PAR1 or PAR4 antibodies, and brought to a total volume of 1 ml in 1×IP buffer. Following a 1 hour incubation at 4° C., appropriate secondary antibody-agarose conjugates were added followed by incubation (30 min with agitation), centrifugation and sufficient washes. The pellets were resuspended in 30 µl of electrophoresis sample buffer and boiled for 5 min. The supernatants were directly used for polyacrylamide sodium dodecyl sulfate gel electrophoresis (SDS-PAGE) and WB analysis. To prepare subcellular fractions of brain samples, we homogenized fresh or fresh-frozen tissues in Tris buffered saline solution (Tris, 10 mM, pH 7.4; NaCl, 150 mM; EDTA, 1 mM; 1 mM EGTA, pH 8.0; 0.2 mM sodium ortho-vanadate) supplemented with protease inhibitor cocktails. After centrifugation (12,000 g at 4° C. for 15 min), the supernatants were collected as cytosolic fractions. The pellets were resuspended in 1×IP buffer containing protease inhibitor cocktail. Following brief sonication and centrifugation (12,000 g at 4° C. for 15 min), the supernatants were collected as membrane fractions. Both antibodies to GRK2 and GRK5 (Santa Cruz) were diluted 1:500 for WB, other routine procedures, WB for total and phospho-p44/42 MAPK, and semi-quantitative analysis of protein band density were performed as previously described (Reference 29).

Measurements of TNF-α Production

TNF-α production in microglial culture media was measured and standardized as previously described (Reference 29).

Immunocytochemistry and Semi-Quantification of GRK Subcellular Distribution

Microglial cells were seeded onto poly-L-lysine-coated 8-chamber slides at a density of $1\times10^4$/well. After various treatments, cells were immediately fixed with pre-chilled (4° C.) 5% acetic acid in methanol for 45 min at 4° C., followed by washing with PBS. The fixed cells were blocked and double-stained with phalloidin-FITC (1:1,000) and anti-GRK5 (1:500) or GRK2 (1:500). Secondary antibody-Cy3 conjugates (1:500) staining, washing, mounting and confocal microscopic visualization were performed routinely as previously described (Reference 29).

Figure 3A:
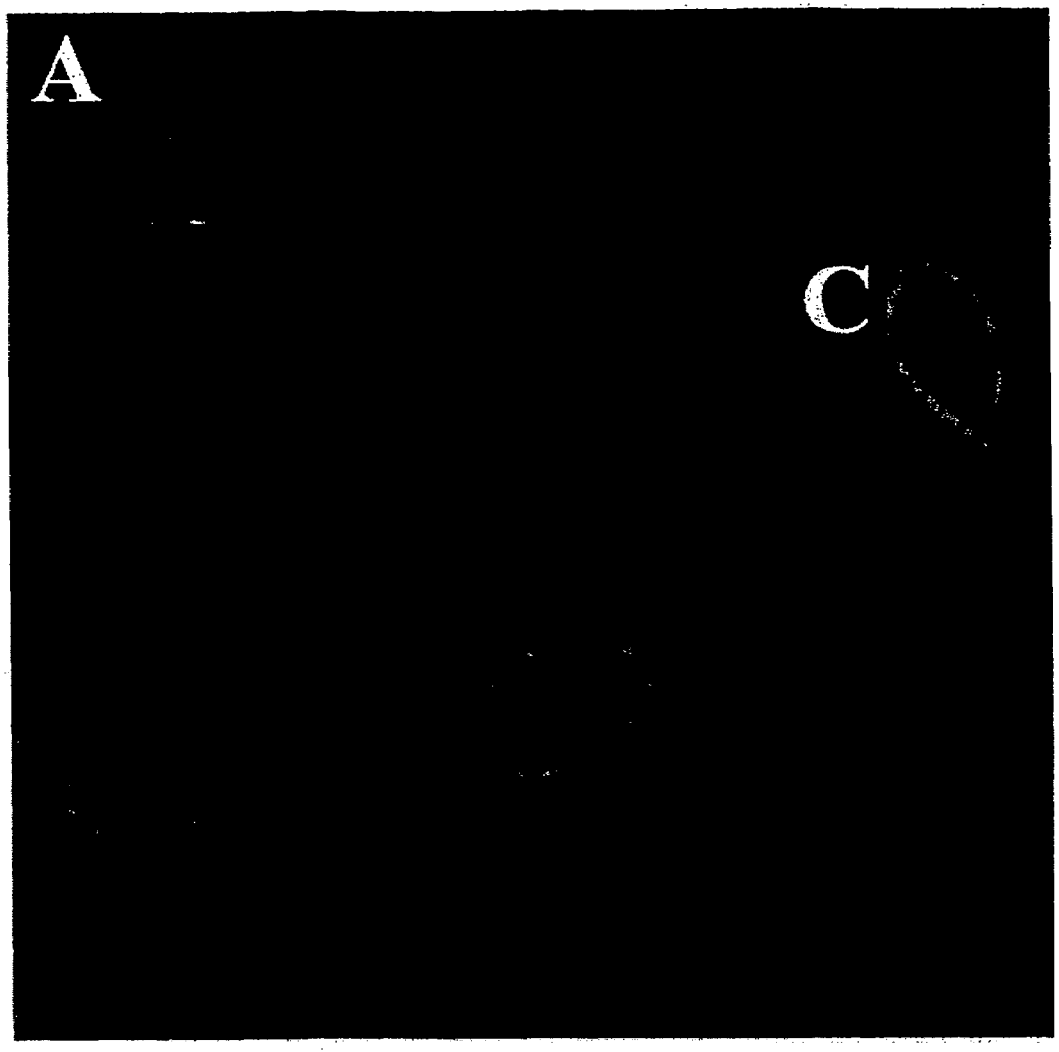
FIGS. 3A-G illustrate sAβ-induced GRK5 translocation from membrane to cytosol in microglia.
Figure 3B:
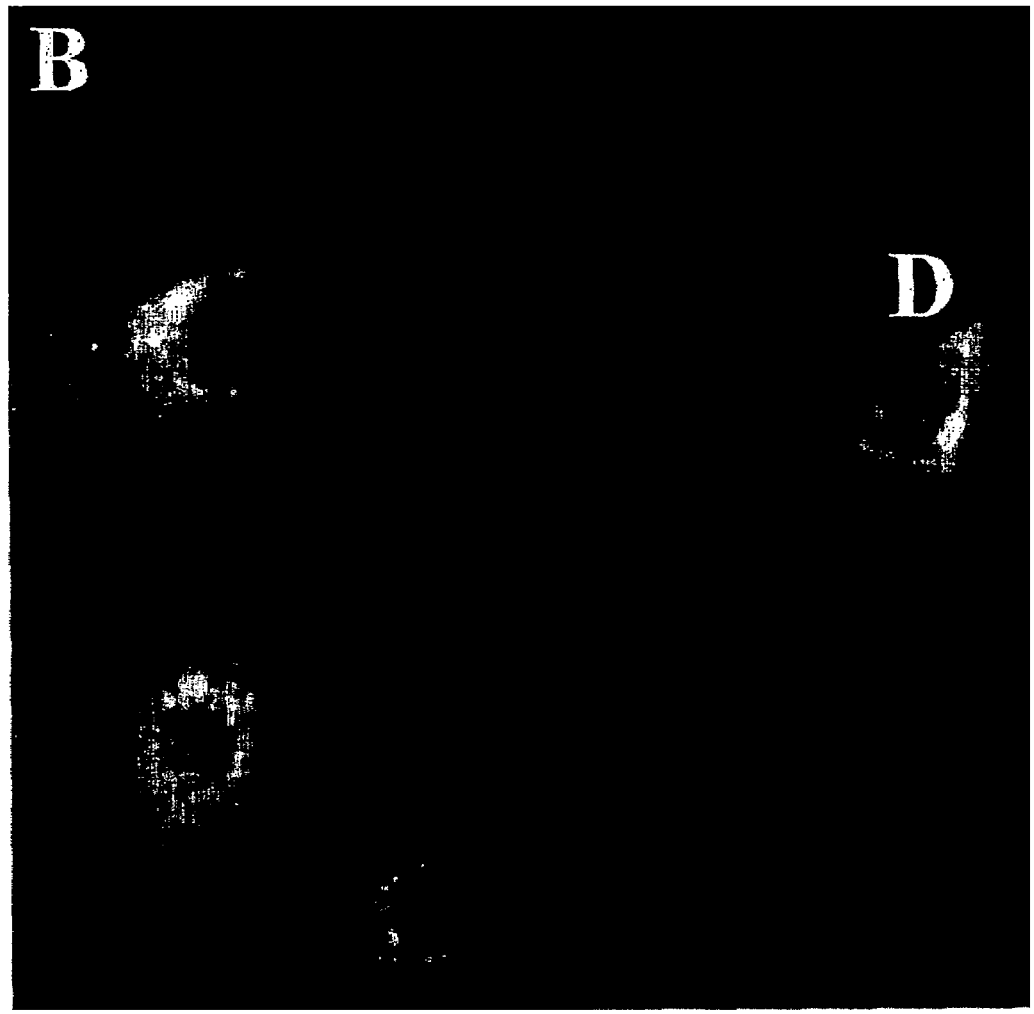
Figure 3C:
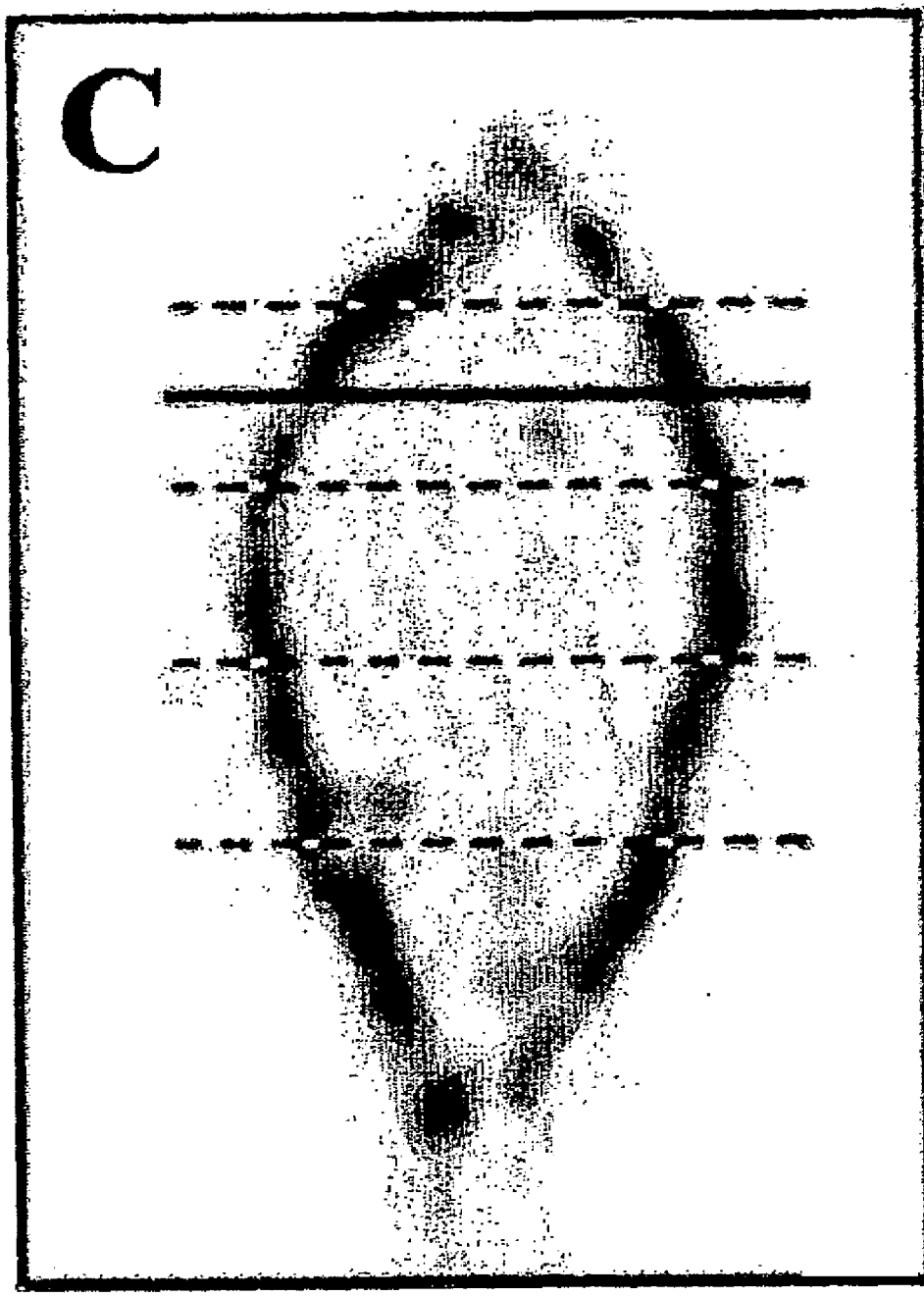
Figure 3D:
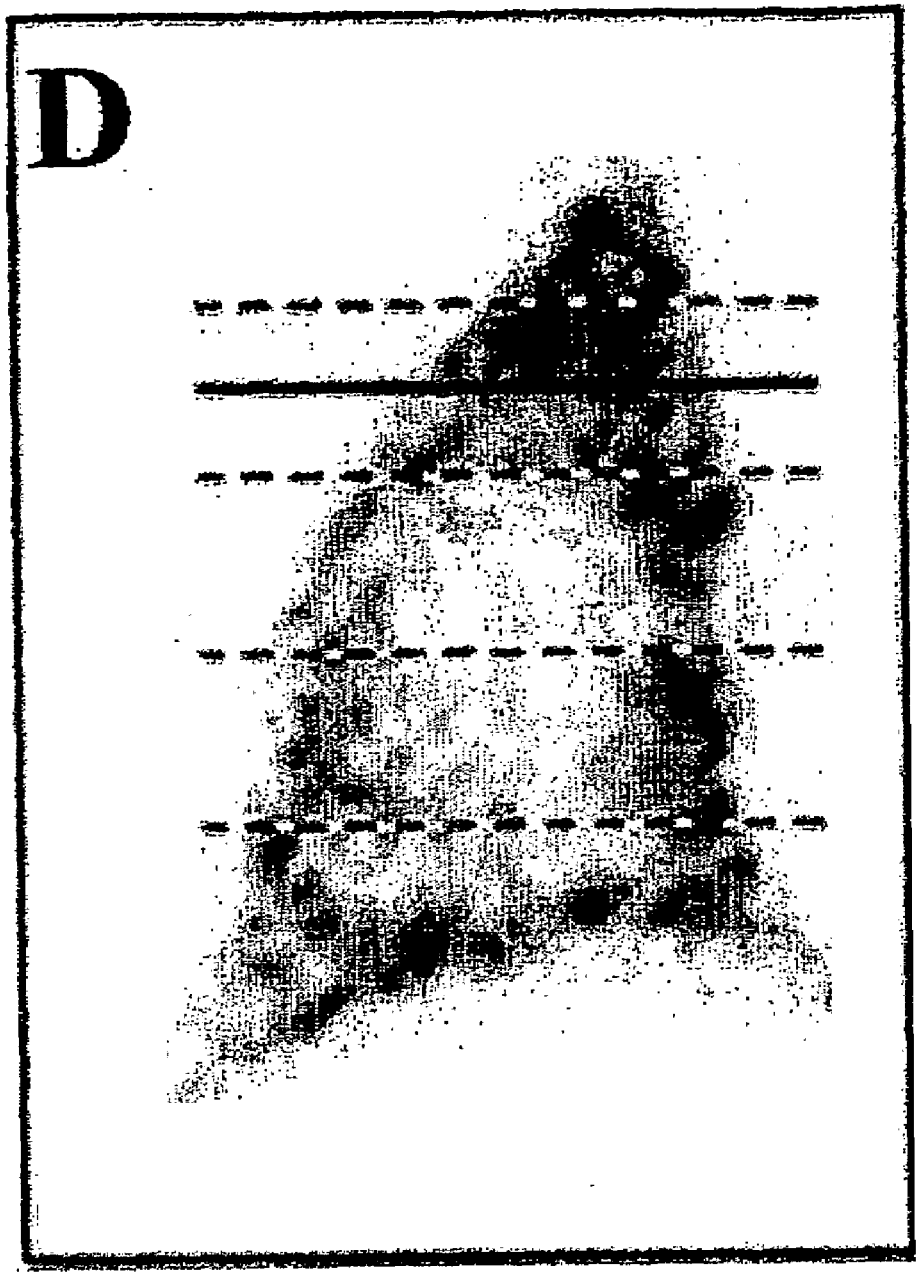
Figure 3E:
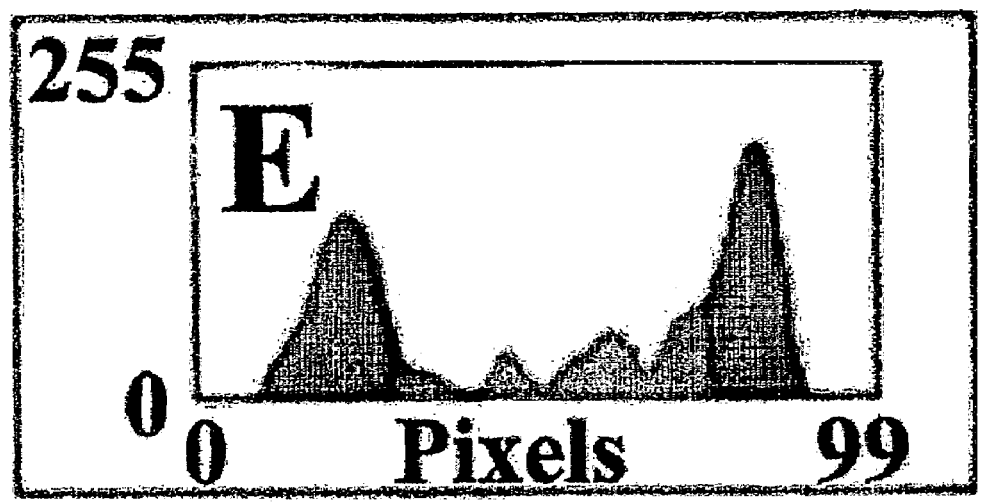
Figure 3F:
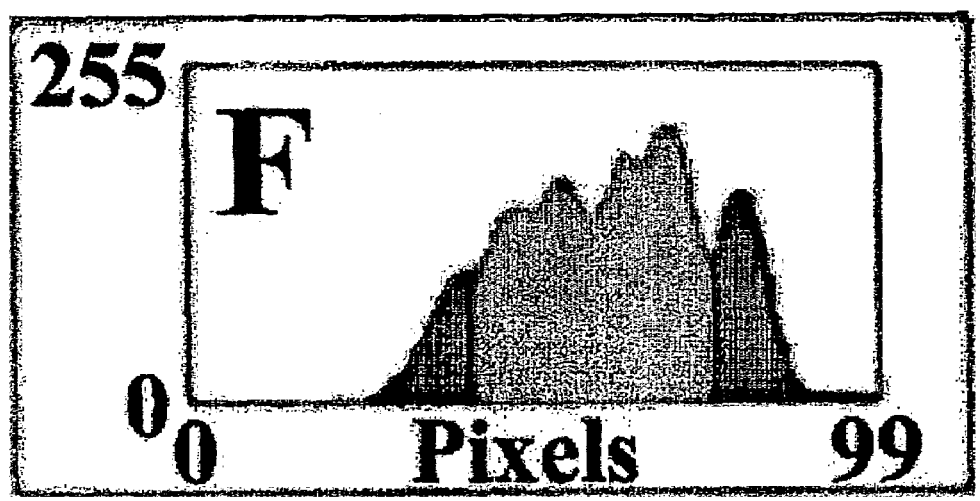
Figure 3G:
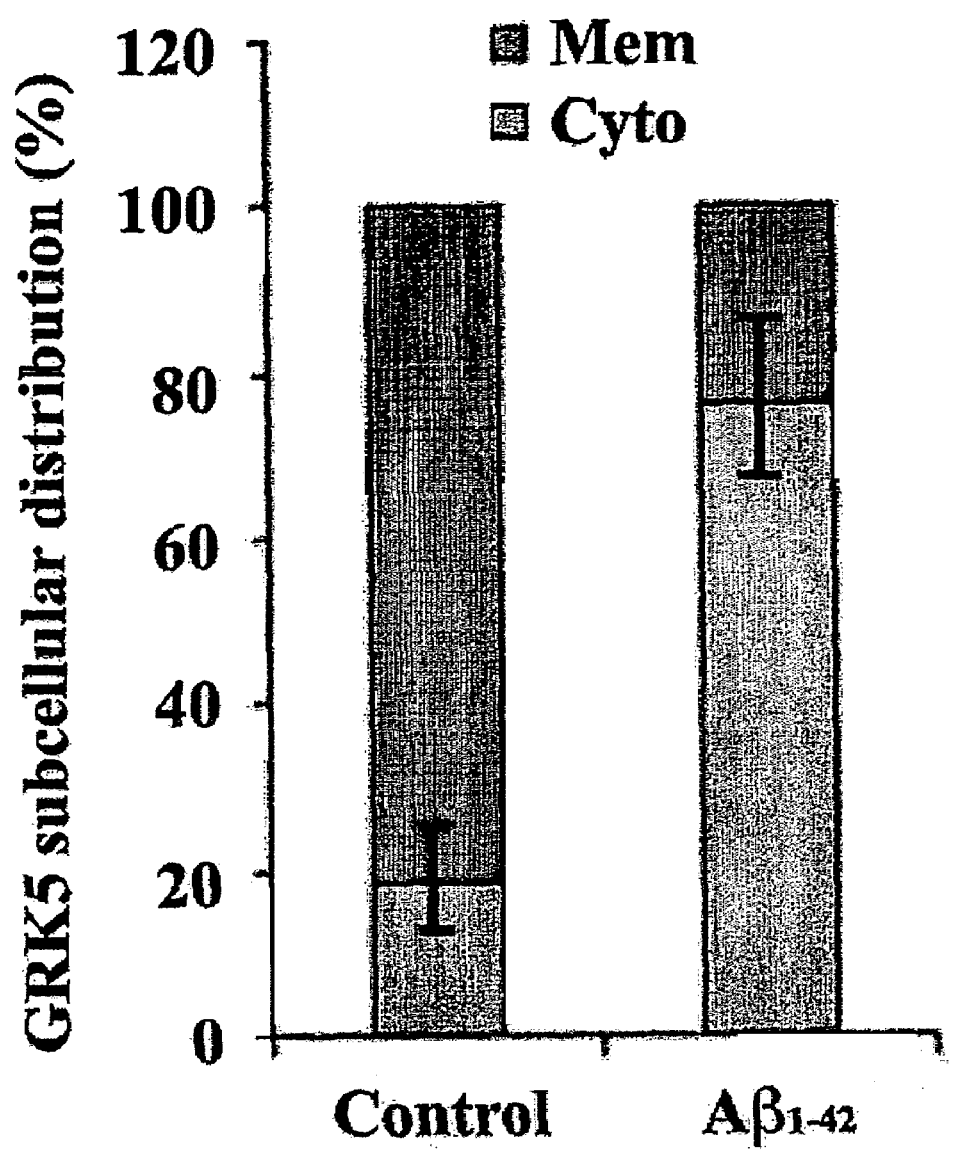

GRK subcellular distribution in sAβ-treated microglial cells were semi-quantified according to a previously-published method (Reference 18) with slight modifications. As shown in FIGS. 3A and B, the dotted-line boxes indicate examples of the cells that were chosen for the semi-quantification. Briefly, the selected cell image corresponding to GRK staining, was copied, enlarged, inverted and rotated to an appropriate position for quantification with NIH Image. As shown in FIGS. 3C and D, linear slices (5-10/each cell) across the cell were profiled to estimate GRK subcellular distribution. FIGS. 3E and F show the examples of profiles for the solid-line indicated levels in FIGS. 3C and D, respectively. The dark and light grey areas in FIGS. 3E and F represent membrane and Cyto, respectively. The sum of areas for membrane and Cyto from all slices in each cell represents GRK subcellular distribution in this particular cell. For each treatment, 20 randomly selected cells were quantified and the average data were shown. FIG. 3G shows the GRK5 subcellular distribution with and without sAβ treatment.

Statistical Analysis

All qualitative experiments (i.e., WB, IP, ICC) were repeated at least three times for each sample or treatment, and all WBs and ICC for GRK5 and GRK2 were also subjected to semi-quantitative analysis to ensure maximal accuracy of the conclusion drawn from these data. Calcium imaging data were averages taken from three separate experiments. TNF-α measurements were repeated once with total n=6 for each treatment. Quantitative data are expressed as mean±S.E.M. and analyzed by ANOVA using StatView 6.0 (Abacus Systems, Mountain View, Calif.). Post-hoc comparisons of means were made using Scheffe's or Tukey's method where appropriate.

Membrane Content for GRK2 and GRK5 is Reduced in AD Brains

We examined the expression and subcellular distribution of GRKs using Western blots (WB) of superior temporal cortical tissue extracts from postmortem brains of AD victims and age-matched non-demented controls. All AD brains conformed to Braak and Braak stage 4 or higher (Reference 1). We found a significant ($p<0.01$) increase of total GRK2 levels in AD brains as compared to the controls. However, the enlarged fraction of GRK2 levels in AD was primarily SDS-resistant high molecular weight aggregates while the monomeric GRK2 appeared decreased ($p<0.01$, FIG. 1A). In contrast, total GRK5 levels in AD brain showed a trend to be decreased, although this was not statistically significant (FIG. 1B). Nonetheless, in the same tissue extracts supplied with sufficient protease inhibitor cocktails, GRK5 consistently displayed several smaller immunopositive bands, implicating a possible GRK5 degradation. Analysis of the subcellular distribution for both GRK2 and GRK5 revealed that the membrane content for GRK2 ($p<0.001$) and GRK5 ($p<0.05$) in AD brains was significantly reduced while the cytosolic GRK2 ($p<0.01$) and GRK5 ($p<0.05$) levels were significantly increased (FIGS. 1C and D). In addition, the subcellular distribution analysis also showed that both GRK2 aggregation and GRK5 degradation that we had found in total tissue extracts appeared limited in the cytosolic fraction. These results suggest that membrane GRKs are likely to be the major functional portion capable of interacting with GPCRs while cytosolic GRK2 and GRK5 appear to more vulnerable to either aggregation or degradation, respectively. Taken together, analyses of postmortem brain tissues revealed a significant reduction of membrane-associated GRK2 and GRK5 in AD as compared to the controls.

GRK Alterations Occur at Prodromal Stages of AD in Tg-CRND8 Mice

Figure 2A:
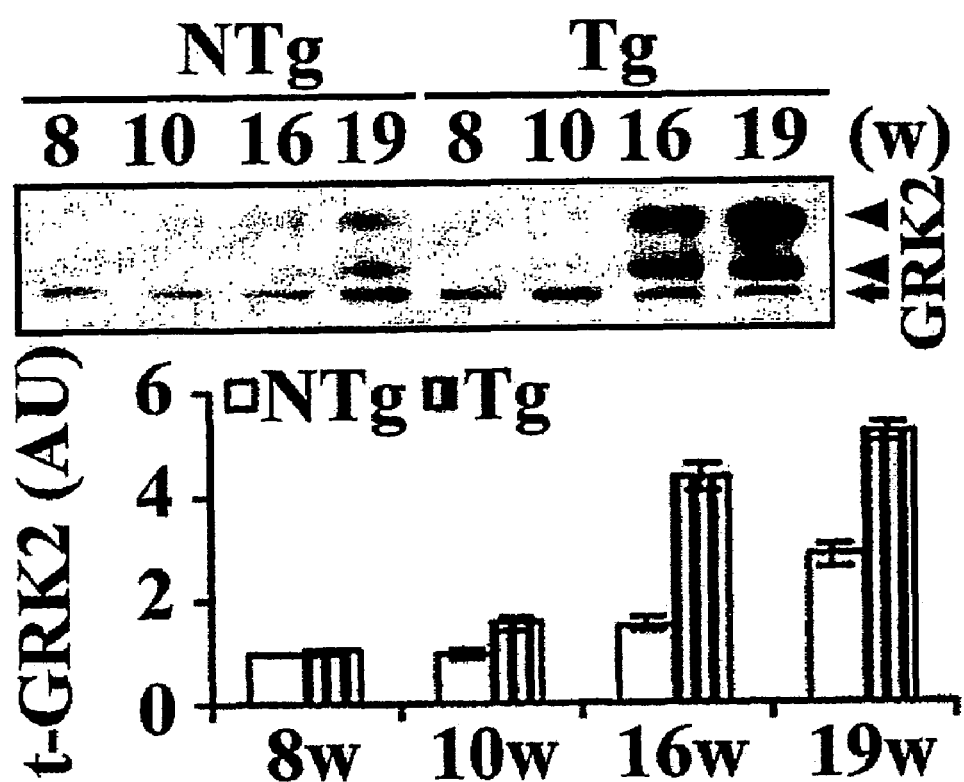
FIGS. 2A-F illustrate expression and subcellular distribution of GRK2 and GRK5 in Tg-CRND8 mouse brains.
Figure 2B:
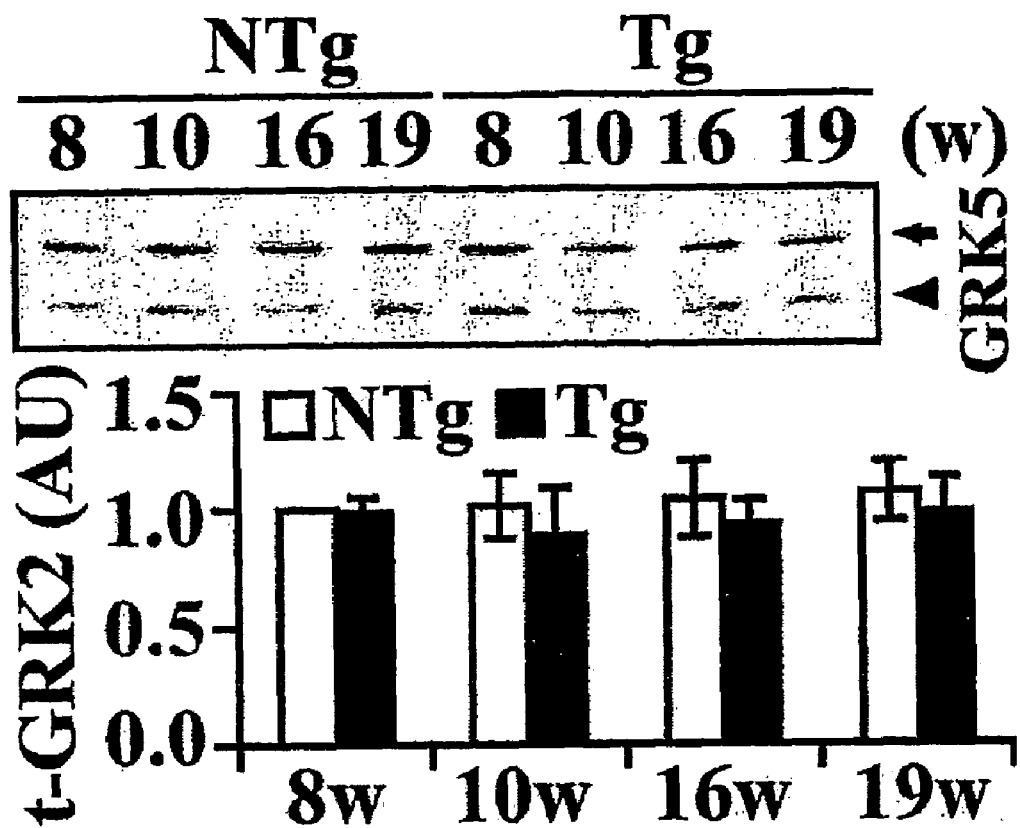

Armed with this novel result in severe postmortem AD, we sought to further assess the significance of GRK alterations in early AD pathogenesis. This was accomplished by analyzing GRK2 and GRK5 subcellular localization in an early-onset AD transgenic mouse line, the Tg-CRND8 mice (Reference 26). Extracts from temporal contices of the Tg-CRND8 mice and their non-transgenic littermates (NTg) were analyzed by WB. Previous studies have shown that total levels of GRK2 and GRK5 in peripheral tissues are differentially regulated by age; GRK2 increases with advancing age while GRK5 does not (Reference 27). To the best of our knowledge, however, changes of GRKs in brain with age have not been previously reported. In this regard, our WB data showed that total brain GRK2 levels increased in mice in an age-dependent manner (within the age groups examined) for both the Tg and NTg animals. However, they were significantly higher in the Tg than in the NTg ($p<0.01$, FIG. 2A). The total GRK2 levels in Tg-CRND8 mice increased significantly at 10 weeks of age ($p<0.05$) and remained significantly upregulated at least until 19 weeks of age ($p<0.01$). Total brain GRK5 levels changed little, if at all, compared to GRK2, where a trend (not statistically significant) to increase with advancing age for the NTg mice was noticed. In turn, total GRK5 levels in the Tg-CRND8 mice decreased significantly ($p<0.05$), beginning at 10 weeks of age (FIG. 2B). The age-dependent changes of GRK2 and GRK5 in mouse brain appeared to agree with that in peripheral tissues (Reference 27). Of interest, increased GRK2 in the Tg mice appeared primarily as high molecular weight aggregates while monomeric GRK2 was significantly reduced as compared to the NTg mice ($p<0.01$), as we had observed in human AD brain. Moreover, such changes appeared to be age-dependent and became more apparent in post-plaque Tg-CRND8 mouse brains. Instead of forming aggregates, low molecular weight GRK5 bands appeared consistently in all groups examined without apparent difference in their intensity. When subcellular fractions were analyzed, we observed a significant decrease of GRK2 and GRK5 in the membrane fraction in Tg-CRND8 mice as early as 7-8 weeks of age ($p<0.05$), while increase of GRK2 and GRK5 was found even earlier, beginning at 5.5 weeks of age ($p<0.001$), as compared to the NTg mice (FIGS. 2C-F). Moreover, this reverse correlation of GRK subcellular distribution in membrane and cytosol fractions persisted in later age groups. Once again, subcellular fraction analysis also confirmed that high molecular weight GRK2 and low molecular weight GRK5 were free from membrane association and limited in cytosolic fractions, supporting the idea that cytosolic GRK2 and GRK5 are vulnerable to aggregation and degradation, respectively. It is worth noting that the Tg-CRND8 mouse line is a model of early onset AD with moderate, but significant increase of brain soluble $A\beta_{1-42}$ ($sA\beta_{1-42}$) levels (both PBS- and SDS-soluble) beginning at 5.5 weeks of age. The dramatic increase of brain $A\beta_{1-42}$ levels appeared at 10 weeks of age, while significant cognitive decline occurs one week later and amyloid plaques were consistently found in all animals at roughly 13 weeks of age (Reference 26). Alterations of GRK subcellular distribution, taking place as early as 5.5 weeks in Tg-CRND8 mice and becoming worse with increased age, corresponded well with the increase in brain $sA\beta_{1-42}$ in vivo. Furthermore, changes in both $sA\beta_{1-42}$ and GRK subcellular distribution in the Tg mice occurred prior to their significant cognitive decline ("disease onset" at ~11 weeks of age), indicating that increased $sA\beta_{1-42}$ and GRK dysfunction may be closely associated with early pathogenetic processes at prodromal stages of AD.

Soluble Aβ has a Direct Impact on GRK Subcellular Distribution

Microglial-mediated inflammation is an important pathological component of AD (Reference 28). To assess whether sAβ has a direct impact on GRK functions, we treated primary murine microglial cells cultured in serum-free medium with $sA\beta_{1-42}$ (0, 50 and 500 nM), $sA\beta_{1-40}$ (0, 50 and 500 nM) and $sA\beta_{40-1}$ (500 nM) for 5 min in the absence or presence of 100 nM α-thrombin for 30 seconds. Thrombin, a serine protease is known to activate protease-activated GPCRs, (PARs) such as PAR1 (Reference 29) and PAR4 in microglia. The sAβ preparation used in this study has been previously characterized as composed principally of conformational intermediates by CD-spectrum (Reference 30) and a mixture of monomeric and oligomeric Aβ by Western blotting. Immunocytochemistry (ICC) staining indicated that 500 nM $sA\beta_{1-42}$ induced a rapid translocation of GRK5 from cell membrane to cytosol (FIGS. 3A-G). To a lesser extent, similar GRK5 changes were also observed for 50 nM $sA\beta_{1-42}$ and 500 nM $sA\beta_{1-40}$ but not for 50 nM $sA\beta_{1-40}$ and 500 nM $sA\beta_{40-1}$. Moreover, as indicated by phalloidin staining, sAβ also caused rapid formation of fibrillar actin (F-actin), and the translocated cytosolic GRK5 partially co-localized with F-actin (FIG. 3B). In addition, when microglial cells were challenged with thrombin, less GRK2 translocation from cytosol to membrane was noted in sAβ-pretreated cells as compared to cells not pretreated. Therefore, these results provide direct evidence indicating that nM sAβ has a significant impact on GRK subcellular distribution in microglial cells.

Figure 4A:
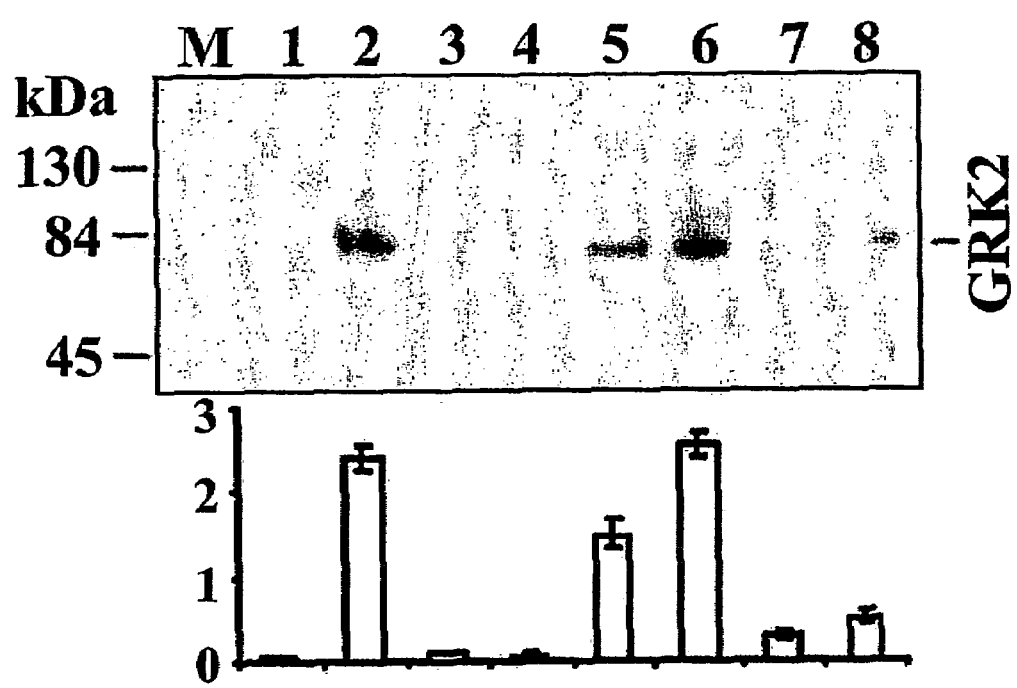
FIGS. 4A-B illustrate inhibition of GRK-PAR binding by sAβ-pretreatment in microglial cells.

Soluble Aβ Inhibits GRK-GPCR Interaction and Results in Prolonged GPCR Signaling Having uncovered the effects of sAβ on GRK subcellular distribution, we further studied the effects of sAβ on GRK-GPCR interactions and the subsequent GPCR signaling changes. Using the same in vitro system described above, we first examined GRK-GPCR (PAR) binding after sAβ and thrombin treatments using immunoprecipitation (IP) and WB. Compared to untreated microglial cells, 30-second treatment with thrombin alone increased binding of PAR1 to GRK5 and GRK2, as well as PAR4 binding to GRK5 and GRK2 by approximately 100, 30, 4 and 2 fold, respectively (FIGS. 4A and B). By contrast, binding of all examined PARs to GRKs was essentially abolished in sAβ-pretreated (5 min) cells. The differential binding between different isoforms of GRKs and PARs agreed with those previously published in other cell types (References 31-32), suggesting that microglial PAR1 is also desensitized primarily by GRK5 and to a lesser extent by GRK2, while PAR4 is barely under significant control by either GRK5 or GRK2. The sAβ-inhibited binding of GRK to PAR was anticipated; however, the degree of the inhibition (completely abolished) was surprising. Taken together, these results strongly suggest that sAβ severely impairs GRK-PAR (GPCR) interactions.

Figure 5A:
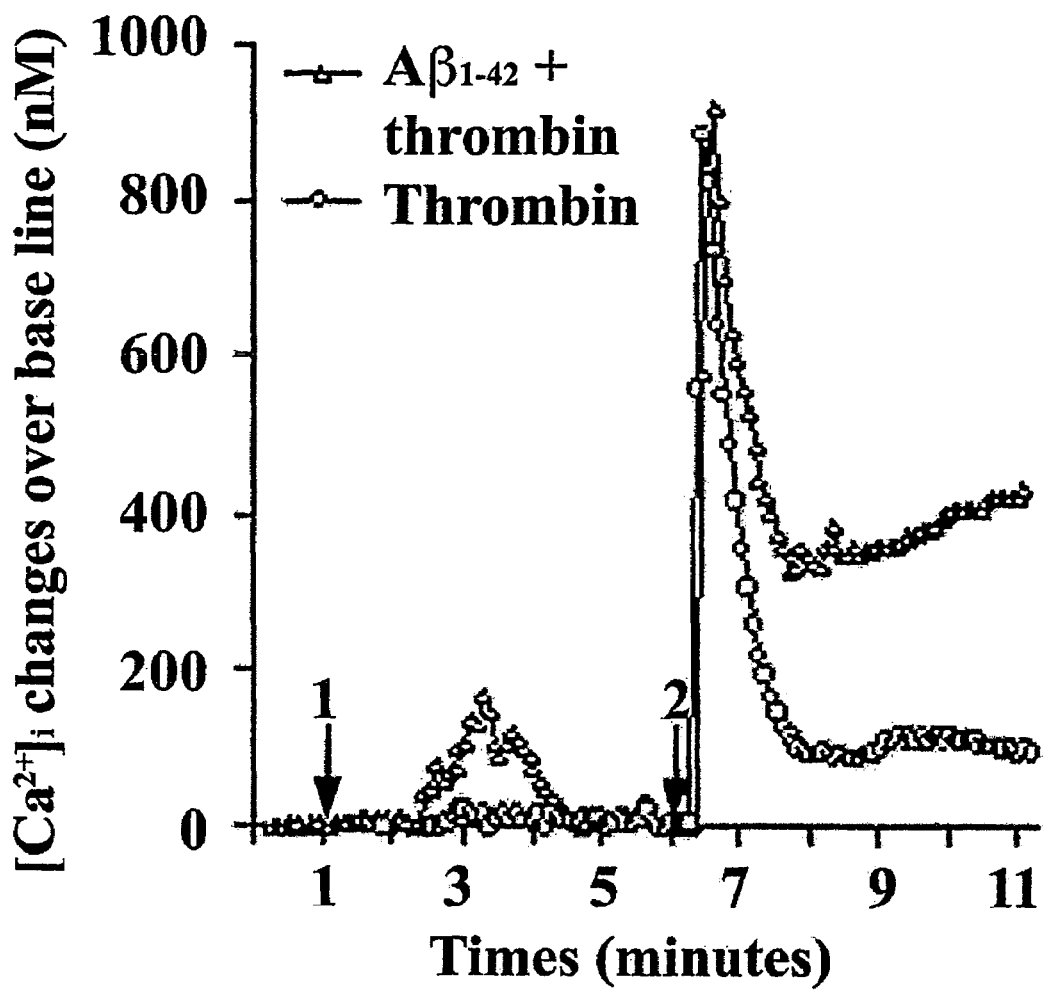
FIGS. 5A-C illustrate that pretreatment with sAβ resulted in prolonged thrombin signaling in microglial cells.

In previous studies, we found thrombin signaling via PARs in microglial cells involving $[Ca^{2+}]_i$ increase and transient activation of both p38 and p44/42 mitogen-activated protein kinases (MAPKs) (Reference 29). To understand potential consequences of GRK dysfunction induced by sAβ, for these studies we also assessed changes in thrombin signaling in sAβ-pretreated microglial cells. We found that sAβ$_{1-42}$ (500 nM) induced a slow and moderate increase of free [Ca$^{2+}$]$_i$ that returned to basal levels within 4 min (FIG. 5A). This was contrasted with the effects of thrombin alone, that induced a steep and sharp increase of [Ca$_{2+}$]$_i$ that rapidly decreased to approximately 100 nM above basal levels and lasted for at least 4 min. In contrast, in sAβ-pretreated cells, thrombin induced a similar [Ca$^{2+}$]$_i$ increase that quickly decreased to ~350 nM above baseline but then slowly climbed to greater than 450 nM without a subsequent decrease (at least within the time observed). The biphasic appearance of these [Ca$^{2+}$]$_i$ data suggest that sAβ pretreatment caused prolongation of the calcium signaling triggered by thrombin in microglial cells. In addition, as indicated by changes in phosphorylation levels of both p44/42 (FIG. 5B) and p38 (FIG. 5C) MAPKs, sAβ, thrombin or sAβ pretreatment (5 min) followed by thrombin, induced increased phosphorylation of the MAPKs within 20 min post-Aβ treatment. By 24 h, both p38 and p44/42 MAPK phosphorylation in sAβ or thrombin alone-treated microglia returned to basal levels. However, in cells with sAβ-pretreatment followed by thrombin, phosphorylation of the p38 and p44/42 MAPKs remained elevated. These data indicate that sAβ pretreatment also caused prolongation of thrombin-induced MAPK activation in microglial cells. Overall, these results suggest that sAβ pretreatment not only inhibits GRK-PAR (GPCR) interactions but also lead to a prolongation of thrombin/PAR signaling in microglial cells.

Soluble Aβ Alters Microglial Reactivity to GPCR Activators

Figure 6A:
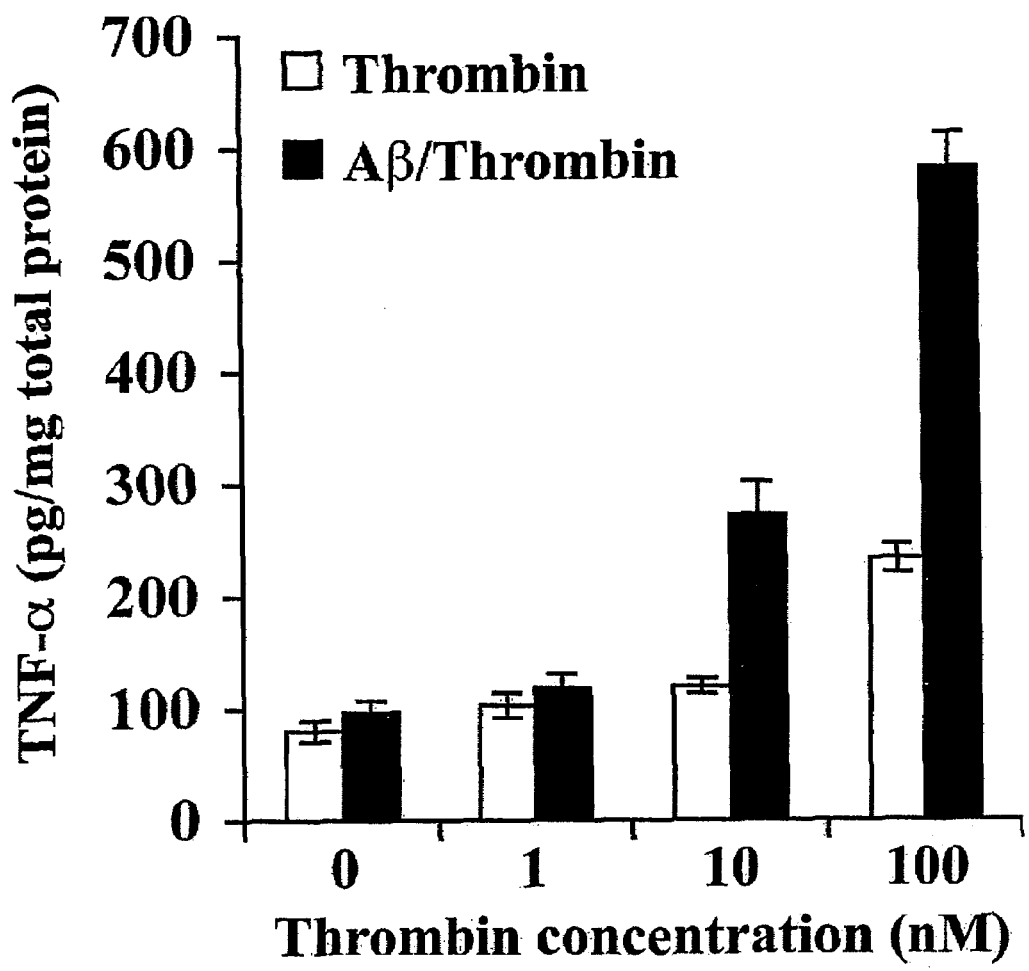
FIGS. 6A-B illustrate sAβ-induced microglial hyper-reactivity to GPCR activators.
Figure 6B:
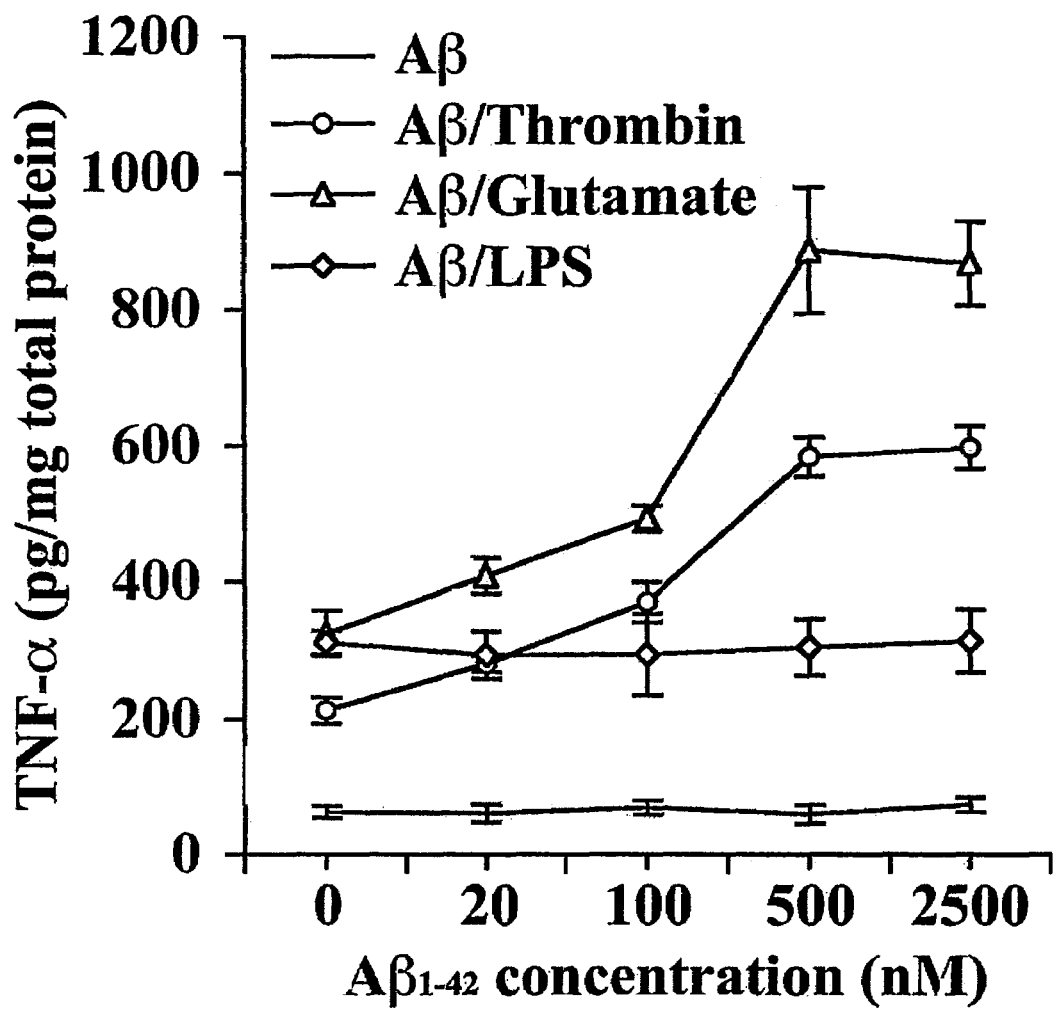

Given our results that sAβ disrupts GRK function and inhibits GPCR desensitization in microglia, we next investigated whether such signaling dysregulation might lead to cellular functional changes in microglia. Both primary and N9 clonal murine microglial cultures were used and TNF-α secretion in culture media was measured as an outcome. We found that nM concentrations of sAβ were insufficient to induce significant TNF-α release in either primary or clonal microglial cultures (FIG. 6). However, a brief (5 min) pretreatment of microglial cells with sAβ significantly potentiated TNF-α release induced by thrombin (FIGS. 6A and B, p<0.01), glutamate (FIG. 6B, p<0.001), but not by lipopolysaccharide (LPS, FIG. 6B). Moreover, the potentiation effect of sAβ on thrombin and glutamate-induced microglial activation was dose-dependent, with a minimal effective concentration (EC$_{min}$) of 20 nM and a maximal EC (EC$_{max}$) of 500 nM. Furthermore, the enhancement effect was not observed if sAβ was given after (10 min) thrombin or glutamate treatments. Since both thrombin (Reference 29) and glutamate (Reference 33) can activate microglia via specific GPCRs while LPS activates microglia via a non-GPCR pathway (Reference 34), these results support the conclusion that sAβ's effects are for specific GPCRs. Together with the evidence that sAβ inhibits GRK-GPCR interactions and causes prolongation of GPCR signaling, we conclude that sAβ, by disrupting GRK function, alters microglial reactivity to specific GPCR activators.

EXAMPLE 1

Expression and Subcellular Distribution of GRK2 and GRK5 in Postmortem AD Brains (FIGS. 1A-D)

Figure 1B:
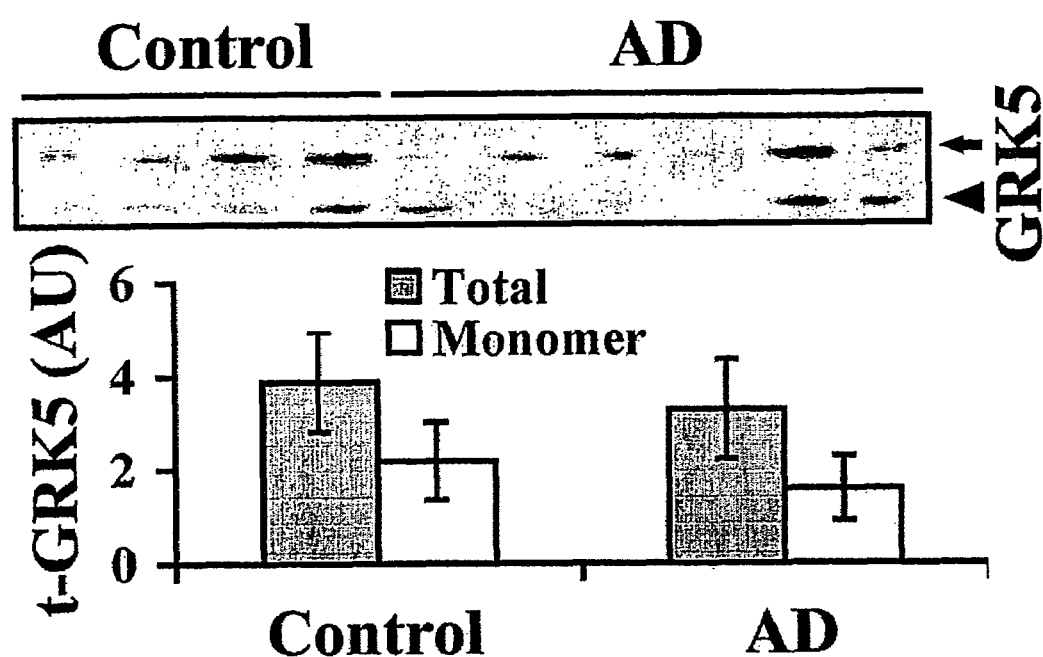
Figure 1C:
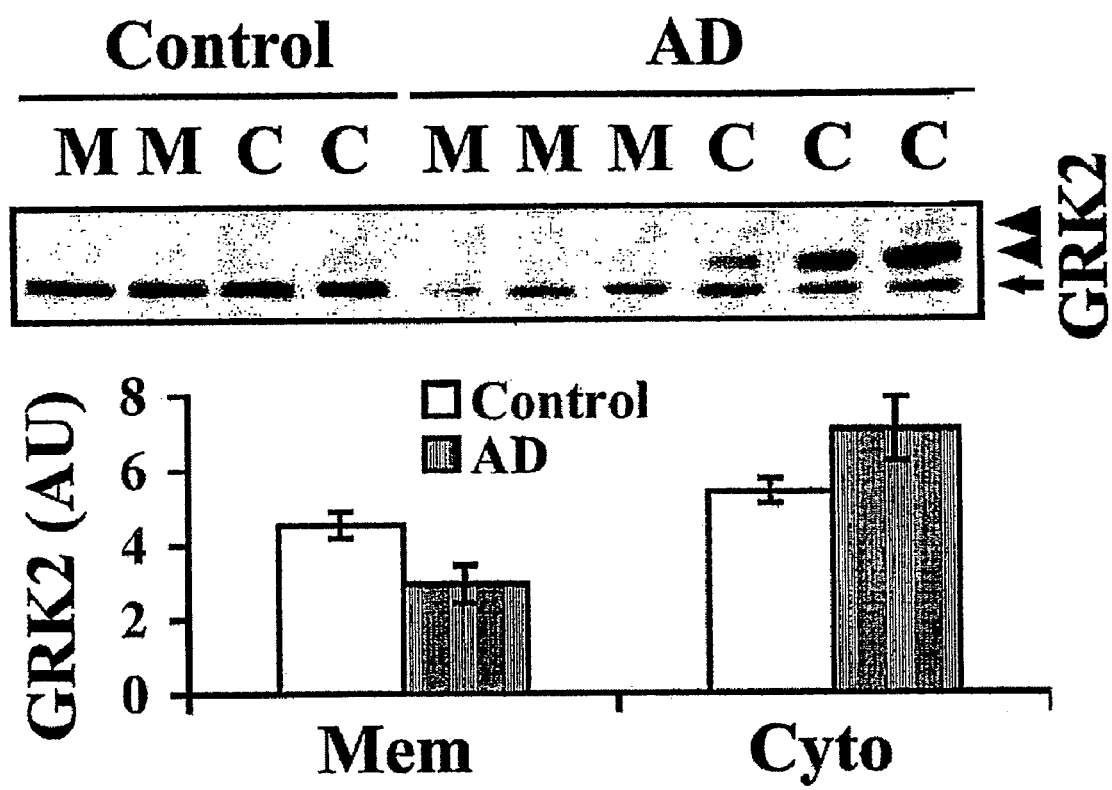
Figure 1D:
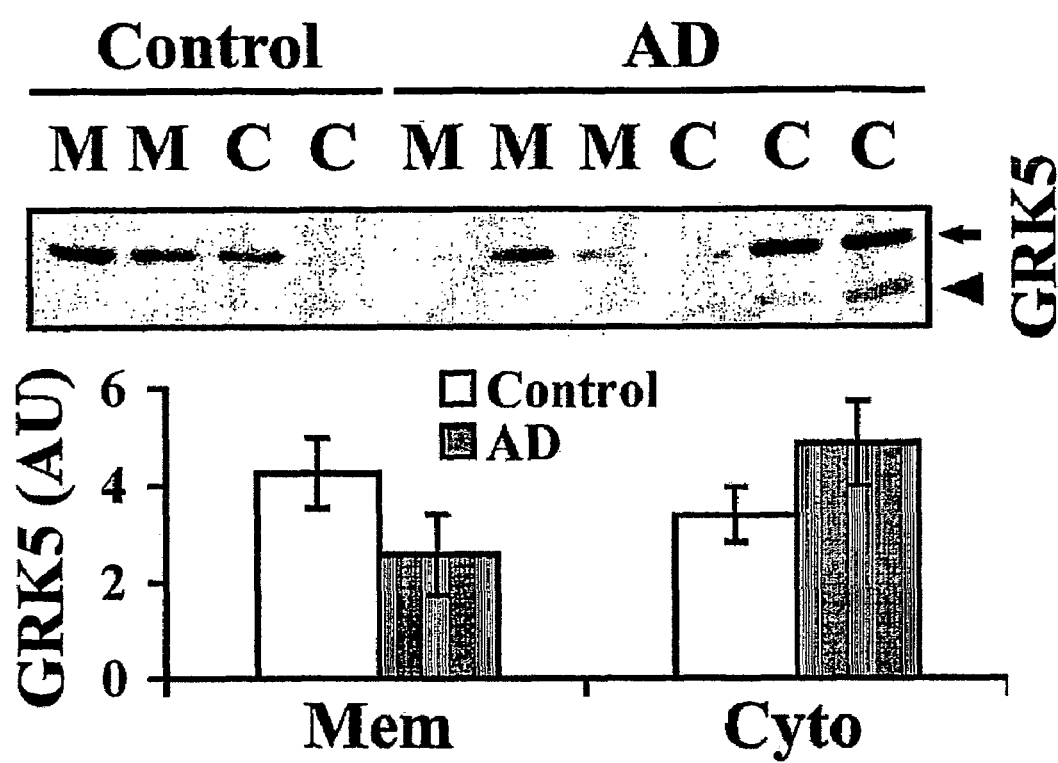

FIGS. 1A-B show total levels of GRK2 and GRK5, respectively, in superior temporal cortices of AD (n=6) and age-matched controls (n=4) analyzed by WB. Arrowheads indicate ~90 and 160 kDa high molecular weight bands consistently seen in GRK2 blots. The total levels of GRK2 (including both monomeric and high molecular weight) were significantly elevated (p<0.01) while the monomeric GRK2 levels were significantly (p<0.01) reduced in AD compared to control. Although both total and monomeric GRK5 levels showed a trend to decrease, neither was statistically significant. FIGS. 1C-D show contents of GRK2 (FIG. 1D) and GRK5 (FIG. 1D) in membrane and cytosolic fractions of the same AD and control samples. Lane M=membrane, C=cytosol. For semi-quantitative analysis, GRK levels in different subcellular fractions were standardized against the means of those for controls (expressed in arbitrary units, AU). As compared to controls, levels of both GRK2 and GRK5 in AD brains were decreased in the membrane fraction (p<0.001 for GRK2 and p<0.05 for GRK5) while they were increased in the cytosol fraction (p<0.01 for GRK2 and p<0.05 for GRK5). Arrow, monomer; arrowhead, oligomers (for GRK2) or fragments (for GRK5).

EXAMPLE 2

Expression and Subcellular Distribution of GRK2 and GRK5 in Tg-CRND8 Mouse Brains (FIGS. 2A-F)

Figure 2C:
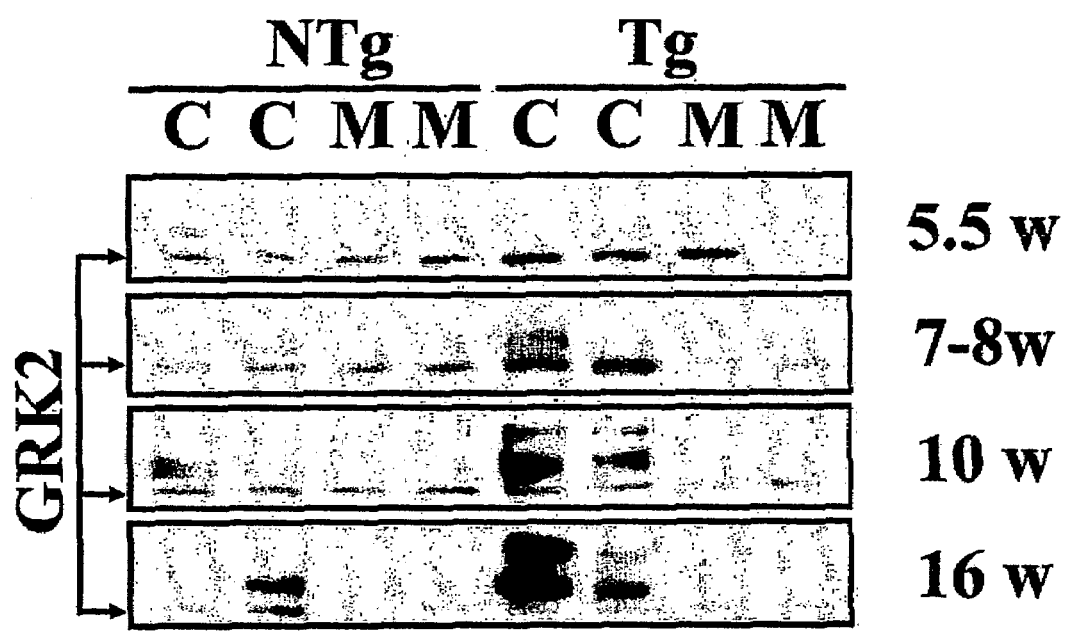
Figure 2D:
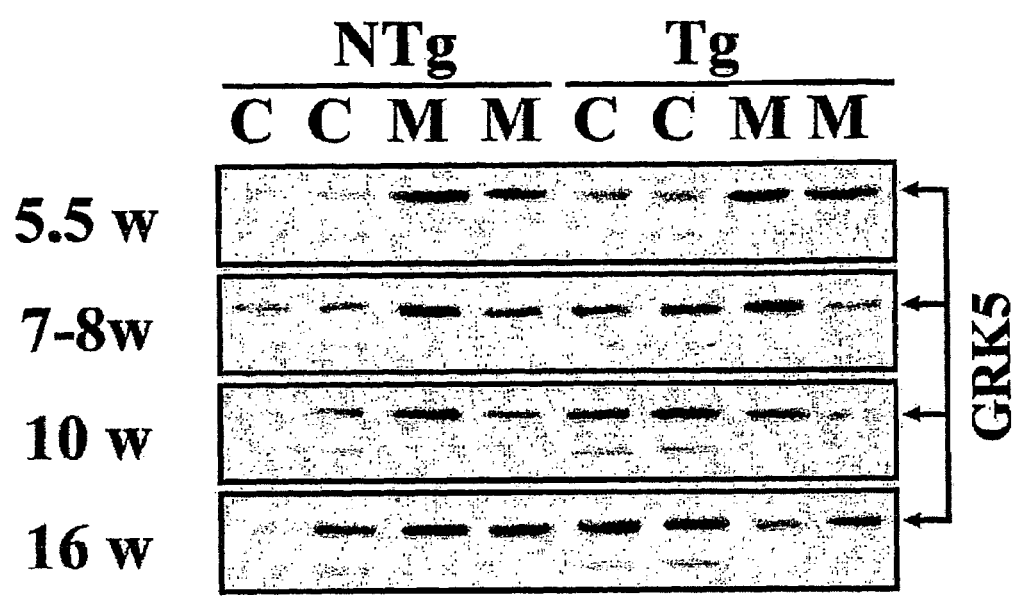
Figure 2E:
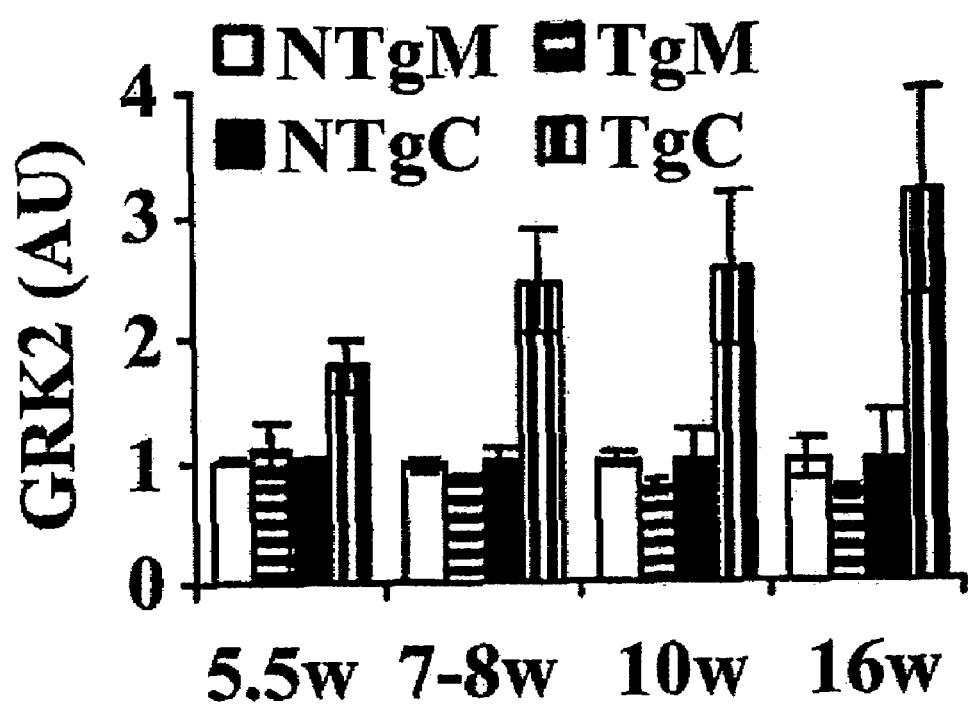
Figure 2F:
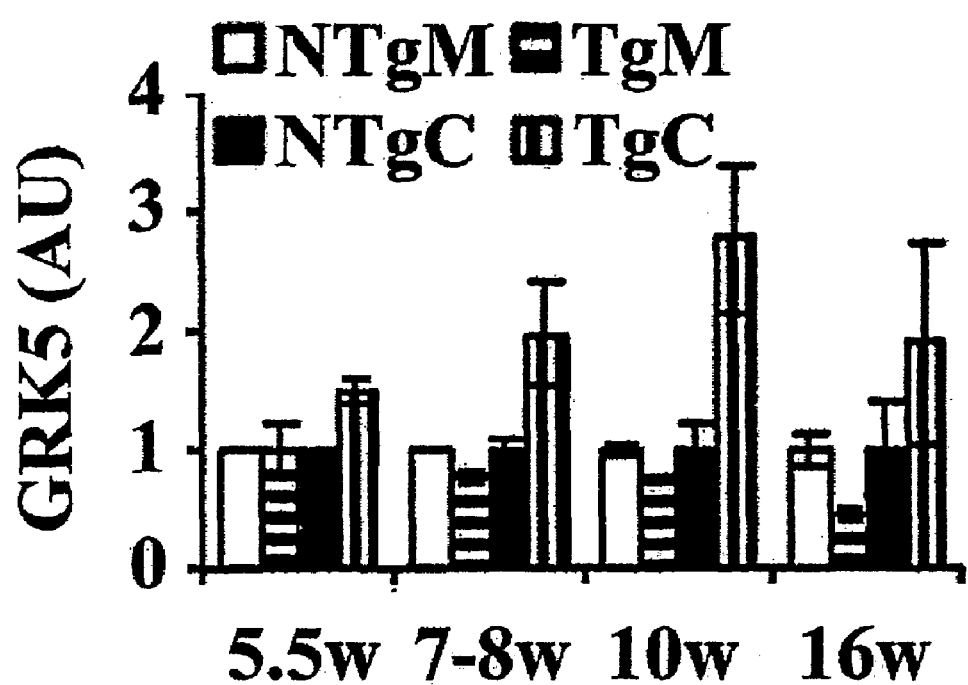

Cortical tissues of Tg-CRND8 mice and their NTg littermates (n≧4 for each group) were used for WB analysis. FIG. 2A shows that total brain GRK2 levels increased in an age-dependent manner (within the age groups examined) for both the Tg and NTg mice, while they were significantly higher in the Tg than in the NTg (p<0.01 by Two way ANOVA). The total GRK2 levels in the Tg mice increased significantly at 10 weeks of age (p<0.05) and remained significantly elevated until at least 19 weeks of age (p<0.01). Total brain GRK5 levels (FIG. 2B) for the NTg mice did not change significantly. Compared to the NTg, although a trend of decrease with advancing age was noticed, such change was not statistically significant. FIGS. 2C, 2D (representative blots) and FIGS. 2E, 2F (corresponding semi-quantitative analysis) show analysis of subcellular distribution of GRK2 and GRK5 in Tg-CRBD8 and NTg mice. Semi-quantitative analysis suggested that significant decrease of GRK2 and GRK5 in the membrane fraction took place at 7-8 weeks old of age (p<0.05) while increase of GRK2 and GRK5 appeared to be more dramatic (p<0.001) and also started earlier at 5.5 weeks old of age. Moreover, this reverse correlation of subcellular distribution of GRKs in membrane and cytosolic fractions remained at later age groups examined. Arrow, monomer; arrowhead, oligomers (for GRK2) or fragments (for GRK5).

EXAMPLE 3 sAβ Induced GRK5 Translocation from Membrane to Cytosol in Microglial (FIGS. 3A-G)

N9 microglial cells were treated with sAβ$_{1-42}$ (500 nM) for 5 minutes. FIGS. 3A, 3C and 3E show resting (control)

microglial cells and corresponding semi-quantitative analysis; FIGS. 3B, 3D, and 3F represent those for sAβ-treated microglial cells and analysis. The detailed methods for semi-quantification of GRK subcellular distribution are described in Methods section (above). ICC with phalloidin-FITC and antibody to GRK5 indicated that sAβ induced a rapid translocation of GRK5 from membrane to cytosol compartment, and the cytosolic GRK5 partially co-localized with F-actin as stained by phalloidin.

EXAMPLE 4

Figure 4B:
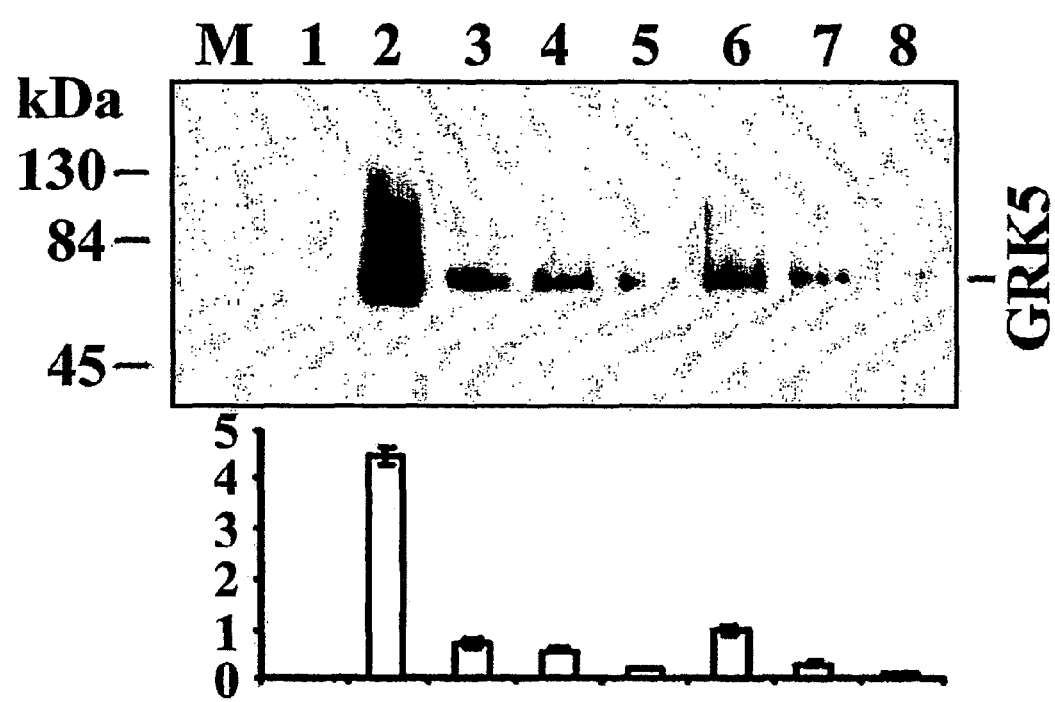

Inhibition of GRK-PAR Binding by sAβ-pretreatment in Microglial Cells (FIGS. 4A-B)

N9 cells were pretreated with sAβ$_{1-42}$ (500 nM) for 5 min, then challenged with 100 nM thrombin for 30 seconds. Cells were immediately lysed for IP and WB analysis. The bar graphs represent averages of three (n=3) repeats of the same experiments. For both FIG. 4A (probed for GRK2) and FIG. 4B (probed for GRK5), lane M=Marker, lane 1-4 were control, thrombin, Aβ$_{1-42}$ and Aβ$_{1-42}$+thrombin, respectively, IP with PAR1 antibody, while lanes 5-8 were the same samples as those in lanes 1-4 but IP with PAR4 antibody. As shown, 30 second thrombin treatment alone increased binding of PAR1-GRK5, PAR1-GRK2, PAR4-GRK5 and PAR4-GRK2 by approximately 90, 30, 4 and 2 folds, respectively. These data suggest that desensitization of PARs in microglia (GRKs-PARs binding), particularly PAR1, appears to be primarily regulated by GRK5 while GRK2 also plays a significant role. Moreover, consistently in all cases, sAβ-pretreatment almost completely abolished PARs-GRKs binding after 30 second-thrombin treatment.

EXAMPLE 5

Figure 5B:
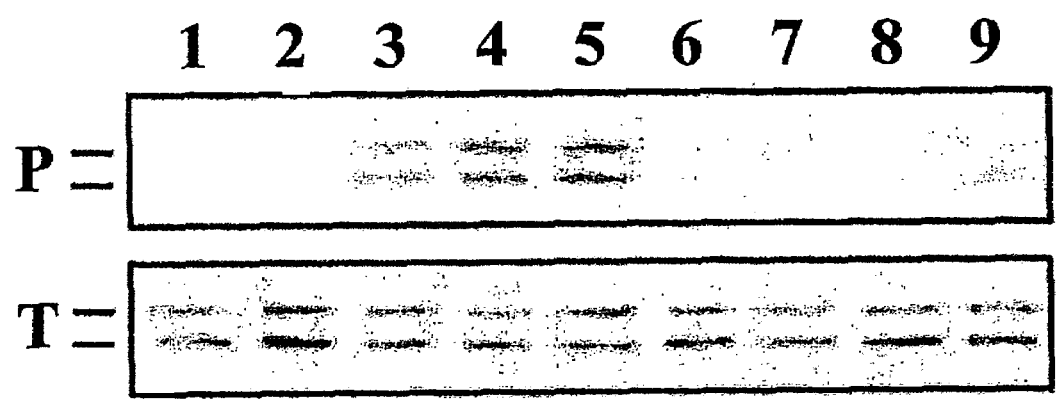

Pretreatment with sAβ Resulted in Prolonged Thrombin Signaling in Microglial Cells (FIGS. 5A-B)

Figure 5C:
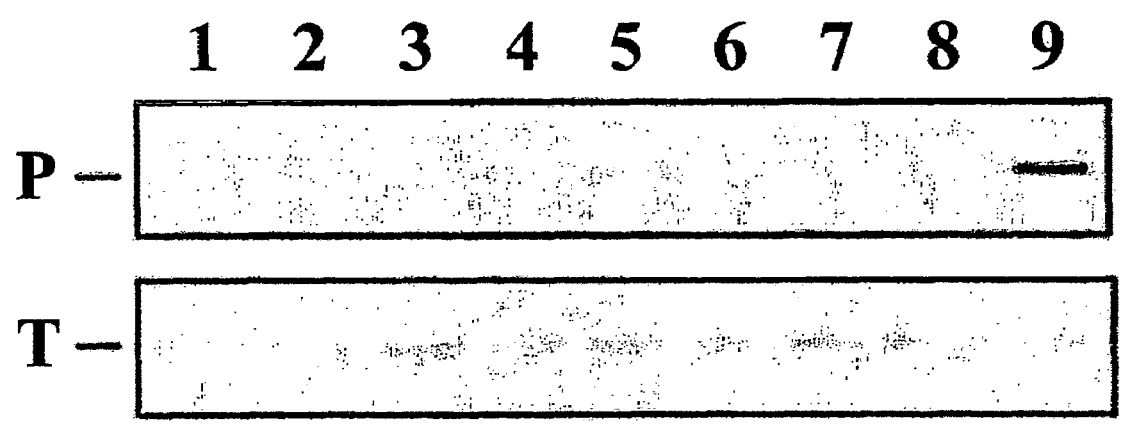

FIG. 5A, N9 microglial cells were pre-treated with 500 nM sAβ$_{1-42}$ (arrow "1") followed by 100 nM thrombin treatment (arrow "2"). Changes in [Ca$^{2+}$]$_i$ were measured as previously described (Reference 29) from three separate experiments. As seen, sAβ$_{1-42}$ induced a slow and moderate increase of free [Ca$^{2+}$]$_i$ but returned to basal levels within 4 minutes. Thrombin alone induced a sharp increase and rapidly decrease of [Ca$^{2+}$]$_i$ while, in sAβ-pretreated cells, thrombin induced a similar level of [Ca$^{2+}$]$_i$ increase but decreased to approximately 350 nM above the basal level and then slowly climbed to greater than 450 nM without decreasing, at least within the time observed. FIG. 5B, sAβ-pretreatment resulted in persistent phosphorylation of p44/42 MAPKs induced by thrombin in N9 microglial cells. FIG. 5C, sAβpretreatment resulted in persistent phosphorylation of p38 MAPK induced by thrombin in N9 microglial cells. For both FIGS. 5B and 5C, lane M=Marker, 1=Control (0 min), 2=Control (25 min), 3=Aβ$_{1-42}$ (25 min), 4=Thrombin (20 min), 5=Aβ$_{1-42}$+thrombin (20 min post-Aβ), 6=Control (24 h), 7=Aβ$_{1-42}$ (24 h), 8=Thrombin (24 h) and 9=Aβ$_{1-42}$+thrombin (24 h post-Aβ). "P" and "T" indicate phosphorylated and total p38 or p44/42 MAPKs, respectively.

EXAMPLE 6 sAβ Induced Microglial Hyper-Reactivity to GPCR Activators (FIGS. 6A-B)

FIG. 6A, pretreatment with sAβ$_{1-42}$ potentiated (p<0.01) TNF-α release induced by increasing doses of thrombin (Thr) as indicated from primary mouse brain microglial cultures. n=4. FIG. 6B, single dose Thr (p<0.001), Glu (p<0.001) and LPS (p<0.001) significantly stimulated TNF-α release in N9 clonal murine microglial cells while sAβ alone was not significant. However, sAβ$_{1-42}$-pretreatment, but not post-treatment (data shown), dose-dependently potentiated effects of Thr (p<0.01) and Glu (p<0.001), but not LPS on TNF-α induction in N9 microglial cells. The EC$_{min}$ and EC$_{max}$ for sAβ's potentiation are approximately 20 nM and 500 nM, respectively. n=6.

Accumulation of soluble Aβ above physiological levels due to GRK dysfunction appears to lead to overamplification and prolonged physiological signaling that may become pathological signaling, causing death of the neurons.

The present discovery provides a means to understand the pathogenetic processes associated with abnormal accumulation of soluble beta-amyloid (Aβ) in early Alzheimer's disease (AD) and to provide guidance for developing specific prognostic, diagnostic, and therapeutic applications.

The present discovery is believed to have the following immediate applications:

Therapeutic Applications

1. The present discovery could lead to correction of the soluble Aβ-induced GRK dysfunction in microglia. This may significantly reduce or eliminate the microglial-mediated inflammatory damage in brain.
2. The present discovery could lead to correction of the soluble Aβ induced GRK dysfunction in neurons. This may significantly reverse the pathology of the signaling pathway, may recover the disrupted functions, and may stop further synaptic and neuronal degeneration.
3. A similar therapy may also ameliorate hypoperfusion in early stages of AD and prevent further cerebrovascular degeneration.

Prognostic Applications

4. GRK dysfunction in peripheral blood cells might be used as the basis to develop prognostic methods that may help to identify high risk populations prior to actual clinical onset of AD.

Diagnostic and Prophylactic Applications

5. The present discovery may help to diagnose AD patients at early stages, which may make the prophylaxis of AD possible.
6. Fibrillar Aβ may function as a GPCR stimulus to exaggerate the inflammatory reaction, therefore an Aβ analog that can stimulate a specific immune reaction against Aβ (without activating the specific GPCR, known as FPLR-1) would be the ideal antigen for Aβ vaccination treatment.

While this invention has been described as having preferred sequences, ranges, steps, materials, structures, features, and/or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

The following references, to the extent that they provide exemplary procedural or other details supplementary to those set forth herein, are specifically incorporated herein by reference.

REFERENCES

1. Braak, H. & Braak, E. Neuropathological stageing of Alzheimer-related changes. *Acta Neuropathol* (Berl) 82, 239-59 (1991).
2. Saitoh, T., Horsburgh, K. & Masliah, E. Hyperactivation of signal transduction systems in Alzheimer's disease. *Ann N Y Acad Sci* 695, 34-41 (1993).
3. Fowler, C. J., Cowburn, R. F., Garlind, A., Winblad, B. & O'Neill, C. Disturbances in signal transduction mechanisms in Alzheimer's disease. *Mol Cell Biochem* 149-150, 287-92 (1995).
4. Joseph, J. A., Cutler, R. & Roth, G. S. Changes in G protein-mediated signal transduction in aging and Alzheimer's disease. *Ann N Y Acad Sci* 695, 42-5 (1993).
5. Shimohama, S. et al. Aberrant phosphoinositide metabolism in Alzheimer's disease. *Ann N Y Acad Sci* 695, 46-9 (1993).
6. Matsushima, H., Shimohama, S., Chachin, M., Taniguchi, T. & Kimura, J. Ca2+-dependent and Ca2+-independent protein kinase C changes in the brain of patients with Alzheimer's disease. *J Neurochem* 67, 317-23 (1996).
7. Mattson, M. P. & Chan, S. L. Dysregulation of cellular calcium homeostasis in Alzheimer's disease: bad genes and bad habits. *J Mol Neurosci* 17, 205-24 (2001).
8. Fowler, C. J., Garlind, A., O'Neill, C. & Cowburn, R. F. Receptor-effector coupling dysfunctions in Alzheimer's disease. *Ann N Y Acad Sci* 786, 294-304 (1996).
9. Hisatomi, O. et al. A novel subtype of G-protein-coupled receptor kinase, GRK7, in teleost cone photoreceptors. *FEBS Lett* 424, 159-64. (1998).
10. Pitcher, J. A., Freedman, N. J. & Lefkowitz, R. J. G protein-coupled receptor kinases. *Annu Rev Biochem* 67, 653-92 (1998).
11. Sallese, M. et al. Regulation of G protein-coupled receptor kinase subtypes by calcium sensor proteins. *Biochim Biophys Acta* 1498, 112-21. (2000).
12. Bristow, M. R. et al. Beta-adrenergic pathways in nonfailing and failing human ventricular myocardium. *Circulation* 82, 112-25 (1990).
13. Ungerer, M., Kessebohm, K., Kronsbein, K., Lohse, M. J. & Richardt, G. Activation of beta-adrenergic receptor kinase during myocardial ischemia. *Circ Res* 79, 455-60 (1996).
14. Gros, R., Benovic, J. L., Tan, G. M. & Feldman, R. D. G-protein-coupled receptor kinase activity is increased in hypertension. *J Clin Invest* 99, 2087-93 (1997).
15. Premont, R. T., Inglese, J. & Lefkowitz, R. J. Protein kinases that phosphorylate activated G protein-coupled receptors. *Faseb J* 9, 175-82 (1995).
16. Chen, J., Makino, C. L., Peachey, N. S., Baylor, D. A. & Simon, M. I. Mechanisms of rhodopsin inactivation in vivo as revealed by a COOH-terminal truncation mutant. *Science* 267, 374-7 (1995).
17. Terwilliger, R. Z., Ortiz, J., Guitart, X. & Nestler, E. J. Chronic morphine administration increases beta-adrenergic receptor kinase (beta ARK) levels in the rat locus coeruleus. *J Neurochem* 63, 1983-6 (1994).
18. Barak, L. S., Warabi, K., Feng, X., Caron, M. G. & Kwatra, M. M. Real-time visualization of the cellular redistribution of G protein-coupled receptor kinase 2 and beta-arrestin 2 during homologous desensitization of the substance P receptor. *J Biol Chem* 274, 7565-9 (1999).
19. Harlan, J. E., Hajduk, P. J., Yoon, H. S. & Fesik, S. W. Pleckstrin homology domains bind to phosphatidylinositol-4,5-bisphosphate. *Nature* 371, 168-70 (1994).
20. DebBurman, S. K., Ptasienski, J., Benovic, J. L. & Hosey, M. M. G protein-coupled receptor kinase GRK2 is a phospholipid-dependent enzyme that can be conditionally activated by G protein betagamma subunits. *J Biol Chem* 271, 22552-62 (1996).
21. Freeman, J. L., Pitcher, J. A., Li, X., Bennett, V. & Lefkowitz, R. J. aipha-Actinin is a potent regulator of G protein-coupled receptor kinase activity and substrate specificity in vitro. *FEBS Lett* 473, 280-4 (2000).
22. Roth, G. S., Joseph, J. A. & Mason, R. P. Membrane alterations as causes of impaired signal transduction in Alzheimer's disease and aging. *Trends Neurosci* 18, 203-6 (1995).
23. Price, D. L. et al. Sequestration of tubulin in neurons in Alzheimer's disease. *Brain Res* 385, 305-10 (1986).
24. Wallace, M. A. Effects of Alzheimer's disease-related beta amyloid protein fragments on enzymes metabolizing phosphoinositides in brain. *Biochim Biophys Acta* 1227, 183-7 (1994).
25. Mattson, M. P. et al. beta-Amyloid peptides destabilize calcium homeostasis and render human cortical neurons vulnerable to excitotoxicity. *J Neurosci* 12, 376-89 (1992).
26. Chishti, M. A. et al. Early-onset amyloid deposition and cognitive deficits in transgenic mice expressing a double mutant form of APP695. *J Biol Chem* 15, 21562-70 (2001).
27. Schutzer, W. E., Reed, J. F., Bliziotes, M. & Mader, S. L. Upregulation of G protein-linked receptor kinases with advancing age in rat aorta. *Am J Physiol Regul Integr Comp Physiol* 280, R897-903 (2001).
28. Griffin, W. S. et al. Glial-neuronal interactions in Alzheimer's disease: the potential role of a 'cytokine cycle' in disease progression. *Brain Pathol* 8, 65-72 (1998).
29. Suo, Z. et al. Participation of protease-activated receptor-1 in thrombin-induced microglial activation. *J Neurochem* 80, 655-66 (2002).
30. Crawford, F. et al. Alzheimer's beta-amyloid vasoactivity: identification of a novel beta-amyloid conformational intermediate. *FEBS Lett* 436, 445-8 (1998).
31. Tiruppathi, C. et al. G protein-coupled receptor kinase-5 regulates thrombin-activated signaling in endothelial cells. *Proc Natl Acad Sci USA* 97, 7440-5 (2000).
32. Shapiro, M. J., Weiss, E. J., Faruqi, T. R. & Coughlin, S. R. Protease-activated receptors 1 and 4 are shut off with distinct kinetics after activation by thrombin. *J Biol Chem* 275, 25216-21. (2000).
33. Noda, M., Nakanishi, H., Nabekura, J. & Akaike, N. AMPA-kainate subtypes of glutamate receptor in rat cerebral microglia. *J Neurosci* 20, 251-8 (2000).
34. Hajjar, A. M., Ernst, R. K., Tsai, J. H., Wilson, C. B. & Miller, S. I. Human Toll-like receptor 4 recognizes host-specific LPS modifications. *Nat Immunol* 3, 354-9 (2002).
35. Stanciu, M. et al. Persistent activation of ERK contributes to glutamate-induced oxidative toxicity in a neuronal cell line and primary cortical neuron cultures. *J Biol Chem* 275, 12200-6 (2000).

36. Iversen, L. L., Mortishire-Smith, R. J., Pollack, S. J. & Shearman, M. S. The toxicity in vitro of beta-amyloid protein. *Biochem J* 311, 1-16 (1995).
37. Meda, L. et al. Activation of microglial cells by beta-amyloid protein and interferon-gamma. *Nature* 374, 647-50 (1995).
38. Lue, L. F. et al. Soluble amyloid beta peptide concentration as a predictor of synaptic change in Alzheimer's disease. *Am J Pathol* 155, 853-62 (1999).
39. Sigurdsson, E. M., Scholtzova, H., Mehta, P. D., Frangione, B. & Wisniewski, T. Immunization with a non-toxic/nonfibrillar amyloid-beta homologous peptide reduces Alzheimer's disease-associated pathology in transgenic mice. *Am J Pathol* 159, 439-47. (2001).
40. Lewis, J. et al. Enhanced neurofibrillary degeneration in transgenic mice expressing mutant tau and APP. *Science* 293, 1487-91 (2001).
41. Sandhu, F. A. et al. NMDA and AMPA receptors in transgenic mice expressing human beta-amyloid protein. *J Neurochem* 61, 2286-9. (1993).
42. Smith, D. H. et al. Brain trauma induces massive hippocampal neuron death linked to a surge in beta-amyloid levels in mice overexpressing mutant amyloid precursor protein. *Am J Pathol* 153, 1005-10 (1998).
43. Aragay, A. M. et al. Monocyte chemoattractant protein-1-induced CCR2B receptor desensitization mediated by the G protein-coupled receptor kinase 2. *Proc Natl Acad Sci USA* 95, 2985-90 (1998).
44. Crawford, F., Suo, Z., Fang, C. & Mullan, M. Characteristics of the in vitro vasoactivity of beta-amyloid peptides. *Exp Neurol* 150, 159-68 (1998).
45. Suo, Z. et al. Soluble Alzheimers beta-amyloid constricts the cerebral vasculature in vivo. *Neurosci Lett* 257, 77-80 (1998).
46. Cowburn R. F., C. O'Neill, W. L. Bonkale, T. G. Ohm, and J. Fastbom. February 2001. Receptor-G-protein signalling in Alzheimer's disease. *Biochemical Society Symposia* 67:163-175.
47. Federal Interagency Forum on Aging-Related Statistics. 2000. Older Americans 2000: Key Indicators of Well-Being.
48. FMG Innovations dba Alzheimer's Test Kit. 2001. Early Alert Alzheimer's Home Screening Test. Apr. 23, 2001.
49. Fraser P. E., G. Yu, L. Levesque, M. Nishimura, D. S. Yang, H. T. J. Mount, D. Westaway, and P. H. St-George-Hyslop. February 2001. Presenilin function: connections to Alzheimer's disease and signal transduction. *Biochemical Society Symposia* 67:89-100.
50. Freeman J. L., E. M. De La Cruz, T. D. Pollard, R. J. Lefkowitz, and J. A. Pitcher. Aug. 7, 1998. Regulation of G protein-coupled receptor kinase 5 (GRK5) by actin. *Journal of Biological Chemistry* 273(32):20653-20657.
51. Market News Publishing Inc. 2001. Nycomed Amersham Imaging and Neurochem collaborate to create Alzheimer's diagnostic. *Intelihealth Inc.* Jul. 19, 2001.
52. McLean C. A., R. A. Cherny, F. W. Fraser, S. J. Fuller, M. J. Smith, K. Beyreuther, A I Bush, and C. L. Masters. December 1999. Soluble pool of Aβ amyloid as a determinant of severity of neurodegeneration in Alzheimer's disease. *Annals of Neurology* 46:860-866.
53. Medical Devicelink. 1997. Test developers pursue early Alzheimer's disease diagnostic. *IVD Technology Magazine*. March 1997.
54. National Institute on Aging. 2001. *Alzheimer's Disease Fact Sheet*. Alzheimer's Disease Education & Referral Center, National Institute on Aging, National Institutes of Health. 2001.
55. National Institutes of Health. 1994. *Alzheimer's Disease*.
56. Neve R. L., D. L. McPhie, and Y. Chen. February 2001. Alzheimer's disease: dysfunction of a signalling pathway mediated by the amyloid precursor protein? *Biochemical Society Symposia* 67:37-50.
57. O'Neill C., R. F. Cowburn, W. L. Bonkale, T. G. Ohm, J. Fastbom, M. Carmody, and M. Kelliher. February 2001. Dysfunctional intracellular calcium homoeostasis: a central cause of neurodegeneration in Alzheimer's disease. *Biochemical Society Symposia* 67:177-194.
58. Pitcher J. A., R. A. Hall, Y. Daaka, J. Zhang, S. S. G. Ferguson, S. Hester, S. Miller, M. G. Caron, R. J. Lefkowitz, and L. S. Barak. May 15, 1998. The G protein-coupled receptor kinase 2 is a microtubule-associated protein kinase that phosphorylates tubulin. *Journal of Biological Chemistry* 273(20):12316-12324.
59. Silva, Chris. 2001. Joining the great chase: Rockville biotech firm is among those racing to find an Alzheimer's cure. *Washington Business Journal*. May 25, 2001.
60. Strittmatter W. J. February 2001. Apolipoprotein E and Alzheimer's disease: signal transduction mechanisms. *Biochemical Society Symposia* 67:101-109.
61. Suo Z., M. Wu, S. Ameenuddin, H. E. Anderson, J. E. Zoloty, B. A. Citron, P. Andrade-Gordon, and B. W. Festoff. February 2002. Participation of protease-activated receptor-1 in thrombin-induced microglial activation. *Journal of Neurochemistry* 80(4):655-666.

What is claimed is:

1. A method of detecting a disruption in normal cellular distribution of a G-protein receptor kinase 5 (GRK5) in a brain cell in vitro, comprising the steps of:
   a) estimating normal distribution of GRK5 in the cell;
   b) treating the cell with soluble beta-amyloid peptide to disrupt normal GRK5 distribution;
   c) estimating GRK5 distribution in the cell after step b);
   d) comparing the data of steps a) and c) to detect disruption in normal GRK5 distribution.

2. The method of claim 1, wherein:
   the disruption occurs in sub-cellular distribution of GRK5.

3. The method of claim 2, wherein:
   the disruption comprises reduction in membrane-associated GRK5.

4. The method of claim 1, wherein:
   the disruption comprises increase in cytosolic GRK5.

5. The method of claim 1, wherein:
   the peptide comprises soluble β-amyloid 1-42 or 1-40.

6. The method of claim 5, wherein:
   the concentration of soluble β-amyloid is in a nM range.

7. The method of claim 5, wherein:
   the concentration of soluble β-amyloid is in a range of about 50 nM-500 nM.

8. The method of claim 1, wherein:
   the brain cell comprises a microglial cell.

9. A method of detecting Alzheimer's pathogenesis in a transgenic mouse with increased soluble Aβ or an Alzheimer's Disease patient comprising measuring the content of G-protein receptor kinase 5 (GRK5) in membrane fractions from the brain of said patient or mouse and comparing the content to that of an unaffected control, wherein a decrease in membrane content of GRK5 indicated Alzheimer's pathogenesis.

10. The method of claim 9, wherein:
    the membrane fractions are obtained from microglial cells.

* * * * *